US012655412B2

(12) United States Patent
Lee et al.

(10) Patent No.: US 12,655,412 B2
(45) Date of Patent: Jun. 16, 2026

(54) PREPHENATE DEHYDRATASE VARIANT AND METHOD OF PRODUCING BRANCHED-CHAIN AMINO ACIDS USING THE SAME

(71) Applicant: CJ CHEILJEDANG CORPORATION, Seoul (KR)

(72) Inventors: Hayun Lee, Seoul (KR); Ju Eun Kim, Seoul (KR); Ji Hye Lee, Seoul (KR); Kyungrim Kim, Seoul (KR); Heeseok Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 280 days.

(21) Appl. No.: 18/275,163

(22) PCT Filed: Jan. 19, 2022

(86) PCT No.: PCT/KR2022/000984
§ 371 (c)(1),
(2) Date: Jul. 31, 2023

(87) PCT Pub. No.: WO2022/164118
PCT Pub. Date: Aug. 4, 2022

(65) Prior Publication Data
US 2024/0384253 A1 Nov. 21, 2024

(30) Foreign Application Priority Data
Feb. 1, 2021 (KR) ........................ 10-2021-0014077

(51) Int. Cl.
*C12N 9/88* (2006.01)
*C12P 13/06* (2006.01)
*C12P 13/08* (2006.01)

(52) U.S. Cl.
CPC ................ *C12N 9/88* (2013.01); *C12P 13/06* (2013.01); *C12P 13/08* (2013.01); *C12Y 402/01051* (2013.01)

(58) Field of Classification Search
CPC . C12N 9/88; C12N 15/77; C12P 13/06; C12P 13/08; C12Y 402/01051; C12R 2001/15
See application file for complete search history.

(56) References Cited

U.S. PATENT DOCUMENTS

| | | | |
|---|---|---|---|
| 8,030,036 B2 | 10/2011 | Van Dien et al. | |
| 8,465,962 B2 | 6/2013 | Kim et al. | |
| 8,859,243 B2 * | 10/2014 | Okutani | C12P 21/02 435/115 |
| 9,109,242 B2 | 8/2015 | Park et al. | |
| 2020/0340022 A1 | 10/2020 | Kwon et al. | |

FOREIGN PATENT DOCUMENTS

| | | |
|---|---|---|
| JP | H05-344881 A | 12/1993 |
| KR | 10-0057684 B1 | 8/1992 |
| KR | 10-1830002 B1 | 2/2018 |
| KR | 10-2143964 B1 | 8/2020 |
| KR | 10-2020-0136813 A | 12/2020 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Hsu et al., "Mutational analysis of feedback inhibition and catalytic sites of prephenate dehydratase from Corynebacterium glutamicum," Arch. Microbiol., 181: 237-244 (2004).
Zhang et al., "Probing the Catalytic Mechanism of Prephenate Dehydratase by Site-Directed Mutagenesis of the *Escherichia coli* P-Protein Dehydratase Domain," Biochemistry, 39: 4722-4728 (2000).
Nelms et al., "Novel Mutations in the pheA Gene of *Escherichia coli* K-12 Which Result in Highly Feedback Inhibition-Resistant Variants of Chorismate Mutase/Prephenate Dehydratase," Applied and Environmental Microbiology, 58(8): 2592-2598 (1992).
Guo et al., "Generation of mutant threonine dehydratase and its effects on isoleucine synthesis in Corynebacterium glutamicum," World Journal of Microbiology and Biotechnology, 31: 1369-1377 (2015).
International Search Report issued in corresponding International Patent Application No. PCT/KR2022/000984 dated May 18, 2022.
GenPept, hypothetical protein HMPREF1287 _01595 [*Corynebacterium* sp. KPL 1986], GenBank: ERS45086.1, [online], retrieved from the Internet , 2013, retrived on Jun. 21, 2024, 2 pages.
GenPept, prephenate dehydratase [Corynebacterium callunae DSM 20147], GenBank: AGG67865.1, [online], retrieved from the Internet 2015, retrieved on Jun. 18, 2024, 1 page.
Office Action issued in corresponding Japanese Patent Application No. 2023-545938, dated Jul. 2, 2024.
UniProt, "Prephenate dehydratase", retrieved from EBI accession No. UNIPROT:E2S3M9, Database accession No. E2S3M9, Jan. 11, 2011.

(Continued)

*Primary Examiner* — Ganapathirama Raghu
(74) *Attorney, Agent, or Firm* — Morgan, Lewis & Bockius LLP

(57) ABSTRACT

Provided is a prephenate dehydratase variant.

14 Claims, No Drawings
Specification includes a Sequence Listing.

(56) References Cited

OTHER PUBLICATIONS

Buchholz et al., "Platform Engineering of Corynebacterium glutamicum with Reduced Pyruvate Dehydrogenase Complex Activity for Improved Production of L-Lysine, 1-Valine, and 2-Ketoisovalerate", Applied and Environmental Microbiology, vol. 79, No. 18, Sep. 2013, pp. 5566-5575.

Extended European Search Report issued in corresponding European Patent Application No. 22746145.6, dated Sep. 25, 2024.

Uniprot, https://www.uniprot.org/uniprotkb/E2S3M9/entry#sequences, E2S3M9, Jan. 11, 2011, 1 page.

Hsu et al., "Mutational analysis of feedback inhibition and catalytic sites of prephenate dehydratase from Corynebacterium glutamicum", Arch Microbial, vol. 181, 2004, pp. 237-244.

NCBI, Multispecies: prephenate dehydratase [Corynebacterium], GenPept, Accession No. WP_003862609 1, Dec. 26, 2019, 1 page.

* cited by examiner

PREPHENATE DEHYDRATASE VARIANT AND METHOD OF PRODUCING BRANCHED-CHAIN AMINO ACIDS USING THE SAME

BACKGROUND OF THE INVENTION

A computer readable text file, entitled "133660-04-9007-US_Sequence_Listing.txt," created on or about Aug. 11, 2023, with a file size of 39,667 bytes contains the sequence listing for this application and is hereby incorporated by reference in its entirety.

FIELD OF THE INVENTION

The present disclosure relates to a prephenate dehydratase variant, and a method of producing branched-chain amino acids using the same.

DESCRIPTION OF THE RELATED ART

L-Amino acids are basic structural units of proteins and used as important materials for pharmaceutical raw materials and food additives, animal feeds, nutrients, pesticides, bactericides, etc. Therefore, industrial production of amino acids has become an economically important industrial process.

Various studies have been made for efficiently producing amino acids, for example, efforts for developing microorganisms producing amino acids with high efficiency or a fermentation process technology. Specifically, target material-specific approaches have been developed, such as increasing the expression of genes encoding enzymes involved in amino acid biosynthesis or removing genes unnecessary for amino acid biosynthesis in the strains of the genus *Corynebacterium* (U.S. Pat. No. 9,109,242 B2, U.S. Pat. No. 8,030,036 B2). In addition to these methods, a method of deleting a gene not involved in amino acid production, and a method of deleting a gene whose specific function in amino acid production is not known are also utilized.

Branched-chain amino acids refer to the three amino acids valine, leucine, and isoleucine, and are known to be mainly metabolized in muscles and to be used as an energy source during activity. As branched-chain amino acids are known to have an important role in maintaining muscles and increasing muscle mass during activity, their consumption is increasing.

SUMMARY OF THE INVENTION

An object of the present disclosure is to provide a prephenate dehydratase variant, in which an amino acid corresponding to position 182 from the N-terminus of an amino acid sequence of SEQ ID NO: 1 is substituted with another amino acid.

Another object of the present disclosure is to provide a polynucleotide encoding the variant and a vector including the same.

Still another object of the present disclosure is to provide a microorganism of the genus *Corynebacterium*, the microorganism including one or more of the variant, the polynucleotide, and the vector.

Still another object of the present disclosure is to provide a method of producing branched-chain amino acids, the method including a step of culturing the microorganism in a medium.

DETAILED DESCRIPTION OF THE PREFERRED EMBODIMENTS

The present disclosure will be described in detail as follows. Meanwhile, each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description described below.

Further, those skilled in the art will recognize, or be able to ascertain using no more than routine experimentation, many equivalents to the specific embodiments of the disclosure described herein. Further, these equivalents should be interpreted to fall within the present disclosure.

An aspect of the present disclosure provides a prephenate dehydratase variant, in which an amino acid corresponding to position 182 from the N-terminus of an amino acid sequence of SEQ ID NO: 1 is substituted with another amino acid.

The prephenate dehydratase variant refers to a variant, in which an amino acid corresponding to the position 182 from the N-terminus of prephenate dehydratase of SEQ ID NO: 1 is substituted with another amino acid in a polypeptide having the prephenate dehydratase activity or in a prephenate dehydratase.

As used herein, the term "prephenate dehydratase" is an enzyme that catalyzes the following reaction.

$$\text{Prephenate} \leftrightarrow \text{Phenylpyruvate} + H_2O + CO_2$$

The prephenate dehydratase of the present disclosure may be a prephenate dehydratase or a polypeptide having the prephenate dehydratase activity, to which a modification for preparing the prephenate dehydratase variant provided in the present disclosure is applied. Specifically, it may be a naturally occurring polypeptide or wild-type polypeptide, or a mature polypeptide thereof, and may include a variant thereof or a functional fragment thereof, but the prephenate dehydratase of the present disclosure may include any one without limitation, as long as it may be a parent of the prephenate dehydratase variant of the present disclosure.

In the present disclosure, the prephenate dehydratase may be, but is not limited to, a polypeptide of SEQ ID NO: 1. In one embodiment, the prephenate dehydratase may be a polypeptide having about 60%, 70%, 75%, 80%, 85%, 90%, 95%, 96%, 97%, 98% or 99% or more sequence identity to the polypeptide of SEQ ID NO: 1, and any one is included within the scope of the prephenate dehydratase, as long as it has the activity identical or corresponding to the polypeptide consisting of the amino acid sequence of SEQ ID NO: 1.

The sequence of the prephenate dehydratase of the present disclosure may be obtained from GenBank of NCBI, which is a known database. Specifically, the prephenate dehydratase may be a polypeptide encoded by pheA gene, but is not limited thereto.

As used herein, the "variant" refers to a polypeptide which has an amino acid sequence different from that of the variant before modification by conservative substitution and/or modification of one or more amino acids but maintains the functions or properties. Such a variant may generally be identified by modifying one or more amino acids of the amino acid sequence of the polypeptide and evaluating the properties of the modified polypeptide. In other words, the ability of the variant may be increased, unchanged, or decreased, as compared to that of the polypeptide before variation. Some variants may include variants in which one or more portions such as an N-terminal leader sequence or a transmembrane domain have been removed. Other variants may include variants in which a portion of the N- and/or C-terminus has been removed from the mature protein. The term "variant" may be used interchangeably with terms such as modification, modified polypeptide, modified protein, mutant, mutein, and divergent, and is not limited thereto as long as it is a term used with the meaning of variation.

Further, the variant may include deletions or additions of amino acids that have minimal effect on the properties and secondary structure of the polypeptide. For example, a signal (or leader) sequence that is co-translationally or post-translationally involved in the protein translocation may be conjugated to the N-terminus of the variant. Further, the variant may be conjugated with other sequences or linkers so as to be identified, purified, or synthesized.

The variant provided in the present disclosure may be the prephenate dehydratase variant in which the amino acid corresponding to position 182 from the N-terminus of the amino acid sequence of SEQ ID NO: 1 is substituted with another amino acid, but is not limited thereto.

The amino acid corresponding to position 182 from the N-terminus of the amino acid sequence of SEQ ID NO: 1 may be arginine.

The variant provided in the present disclosure may include a substitution of the amino acid corresponding to position 182 from the N-terminus of the amino acid sequence of SEQ ID NO: 1 with another amino acid other than arginine, but is not limited thereto.

The "another amino acid" is not limited as long as it is an amino acid different from the amino acid before substitution. On the other hand, when expressed as being 'substituted with a specific amino acid' in the present disclosure, it is obvious that the amino acid is substituted with an amino acid different from the amino acid before substitution, even though it is not separately indicated that the amino acid is substituted with a different amino acid.

In one embodiment, the variant of the present disclosure may be a variant, in which the amino acid corresponding to position 182 in the amino acid sequence of SEQ ID NO: 1, which is a reference protein, is substituted with an amino acid different from the amino acid before substitution, among hydrophobic amino acids or aliphatic amino acids.

Specifically, the variant may be a variant in which the amino acid corresponding to position 182 in the amino acid sequence of SEQ ID NO: 1 is substituted with one amino acid of hydrophobic (non-polar) amino acids or aliphatic amino acids. The aliphatic amino acid may be, for example, an amino acid selected from the group consisting of glycine, alanine, valine, leucine, and isoleucine, but is not limited thereto. The hydrophobic (non-polar) amino acid may be, for example, an amino acid selected from the group consisting of glycine, methionine, alanine, valine, leucine, isoleucine, proline, phenylalanine, tyrosine, and tryptophan, but is not limited thereto.

In one embodiment, the variant of the present disclosure may be a variant, in which the amino acid corresponding to position 182 in the amino acid sequence of SEQ ID NO: 1 is substituted with an amino acid different from the amino acid before substitution, among small-size amino acids, but is not limited thereto.

As used herein, the term "small-size amino acid" includes glycine, alanine, serine, threonine, cysteine, valine, leucine, isoleucine, proline, and asparagine, which are relatively small amino acids among 20 amino acids, and specifically, it may refer to glycine, alanine, serine, threonine, cysteine, valine, leucine, isoleucine, and proline, but is not limited thereto. More specifically, it may refer to glycine, alanine, valine, leucine, isoleucine, serine, and threonine, for example, alanine, serine, glycine, but is not limited thereto.

More specifically, in the variant of the present disclosure, substitution with another amino acid may be substitution with alanine, but is not limited thereto.

As used herein, the term "corresponding to" refers to amino acid residues at positions listed in the polypeptide, or amino acid residues that are similar, identical, or homologous to those listed in the polypeptide. Identifying the amino acid at the corresponding position may be determining a specific amino acid in a sequence that refers to a specific sequence. As used herein, "corresponding region" generally refers to a similar or corresponding position in a related protein or a reference protein.

For example, an arbitrary amino acid sequence is aligned with SEQ ID NO: 1, and based on this, each amino acid residue of the amino acid sequence may be numbered with reference to the amino acid residue corresponding to the amino acid residue of SEQ ID NO: 1. For example, a sequence alignment algorithm as described in the present disclosure may determine the position of an amino acid or the position at which modification such as substitution, insertion, or deletion occurs through comparison with that in a query sequence (also referred to as a "reference sequence").

For such alignments, for example, the Needleman-Wunsch algorithm (Needleman and Wunsch, 1970, J. Mol. Biol. 48:443-453), the Needleman program of EMBOSS package (EMBOSS: The European Molecular Biology Open Software Suite, Rice et al., 2000, Trends Genet. 16:276-277) and the like may be used, but are not limited thereto, and a sequence alignment program, a pairwise sequence comparison algorithm, etc., known in the art, may be appropriately used.

In one embodiment, the variant of the present disclosure may have about 60%, 70%, 75%, 80%, 85%, 90%, 95%, 96%, 97%, 98%, or 99% or more sequence identity to the polypeptide of SEQ ID NO: 1, in which the amino acid corresponding to position 182 of SEQ ID NO: 1 is substituted with another amino acid.

In one embodiment, the variant of the present disclosure may include an amino acid sequence having at least 70%, 75%, 80%, 85%, 90%, 95%, 96%, 97%, 98%, 99%, 99.5%, 99.7% or 99.9% or more homology or identity to an amino acid sequence described by SEQ ID NO: 5.

Specifically, the variant of the present disclosure may have, comprise, or consist of the amino acid sequence described by SEQ ID NO: 5, or may essentially consist of the amino acid sequence.

In one embodiment, the variant of the present disclosure may include an amino acid sequence having alanine as an amino acid corresponding to position 182, based on the amino acid sequence of SEQ ID NO: 1, and having at least 70%, 75%, 80%, 85%, 90%, 95%, 96%, 97%, 98%, 99%, 99.5%, 99.7% or 99.9% or more homology or identity to the amino acid sequence described by SEQ ID NO: 5. Further, it is apparent that variants having amino acid sequences in which some sequences are deleted, modified, substituted, conservatively substituted, or added are also included in the scope of the present disclosure as long as the amino acid sequences have such homology or identity and exhibit efficacy corresponding to that of the variant of the present disclosure.

For example, the variant may include those having addition or deletion of a sequence that do not alter the function of the variant of the present disclosure, at the N-terminus, C-terminus, and/or inside of the amino acid sequence, or a naturally occurring mutation, a silent mutation, or a conservative substitution.

The "conservative substitution" means substitution of one amino acid with another amino acid having similar structural and/or chemical properties. Such an amino acid substitution may generally occur based on similarity in the polarity, charge, solubility, hydrophobicity, hydrophilicity, and/or amphipathic nature of residues. Usually, conservative substitution may hardly affect or not affect activity of proteins or polypeptides.

As used herein, the term 'homology' or 'identity' means the degree of similarity between two given amino acid sequences or base sequences and may be expressed as a percentage. The terms 'homology and identity' may often be used interchangeably.

The sequence homology or identity of a conserved polynucleotide or polypeptide is determined by standard alignment algorithms, and the default gap penalty established by a program used may be used together. Substantially, homologous or identical sequences are generally capable of being hybridized with the entirety or a part of the sequence under moderately or highly stringent conditions. It is apparent that hybridization also includes hybridization of a polynucleotide with a polynucleotide including a general codon or a codon in consideration of codon degeneracy.

Whether any two polynucleotide or polypeptide sequences have homology, similarity, or identity may be determined using known computer algorithms such as the "FASTA" program, for example, using default parameters as in Pearson et al (1988) [Proc. Natl. Acad. Sci. USA 85]: 2444. Alternatively, the homology, similarity, or identity may be determined using Needleman-Wunsch algorithm (Needleman and Wunsch, 1970, J. Mol. Biol. 48:443-453) as performed in the Needleman program of the EMBOSS package (EMBOSS: The European Molecular Biology Open Software Suite, Rice et al., 2000, Trends Genet. 16:276-277) (version 5.0.0 or later) (including GCG program package (Devereux, J., et al., Nucleic Acids Research 12:387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.] (1988) SIAM J Applied Math 48:1073). For example, BLAST of the National Center for Biotechnology Information or ClustalW may be used to determine the homology, similarity, or identity.

The homology, similarity, or identity of polynucleotides or polypeptides may be determined by comparing sequence information using, for example, a GAP computer program such as Needleman et al. (1970), J Mol Biol. 48:443, as announced in, for example, Smith and Waterman, Adv. Appl. Math (1981) 2:482. In summary, the GAP program may be defined as the value acquired by dividing the number of similarly aligned symbols (namely, nucleotides or amino acids) by the total number of symbols in the shorter of two sequences. The default parameters for the GAP program may include (1) a binary comparison matrix (including values of 1 for identity and 0 for non-identity) and a weighted comparison matrix of Gribskov et al (1986) Nucl. Acids Res. 14:6745 (or EDNAFULL (EMBOSS version of NCBI NUC4.4) substitution matrix) as disclosed in Schwartz and Dayhoff, eds., Atlas Of Protein Sequence And Structure, National Biomedical Research Foundation, pp. 353-358 (1979); (2) a penalty of 3.0 for each gap and an additional 0.10 penalty for each symbol in each gap (or gap opening penalty of 10, gap extension penalty of 0.5); and (3) no penalty for end gaps.

In one embodiment, the variant of the present disclosure may have the prephenate dehydratase activity. In one embodiment, the variant of the present disclosure may have an activity to increase the productivity of branched-chain amino acids, as compared to the wild-type or unmodified prephenate dehydratase. In one embodiment, the variant of the present disclosure may have an activity to decrease the production level of by-products in the branched-chain amino acid production pathway, as compared to the wild-type or unmodified prephenate dehydratase. In one embodiment, the variant of the present disclosure may have a weakened activity, as compared to the wild-type or unmodified prephenate dehydratase, but is not limited thereto.

Another aspect of the present disclosure provides a polynucleotide encoding the variant of the present disclosure.

As used herein, the term "polynucleotide" is a DNA or RNA strand having a certain length or more as a polymer of nucleotides in which nucleotide monomers are connected in a long chain by covalent bonds, and more specifically, it means a polynucleotide fragment encoding the variant.

The polynucleotide encoding the variant of the present disclosure may include a nucleotide sequence encoding the amino acid sequence described by SEQ ID NO: 5. In one embodiment of the present disclosure, the polynucleotide of the present disclosure may have or include a sequence of SEQ ID NO: 6. Further, the polynucleotide of the present disclosure may consist of or essentially consist of the sequence of SEQ ID NO: 6.

In the polynucleotide of the present disclosure, various modifications may be made in the coding region as long as the amino acid sequence of the variant of the present disclosure is not changed, in consideration of codon degeneracy or codons preferred in organisms that are intended to express the variant of the present disclosure. Specifically, the polynucleotide of the present disclosure may have or include a nucleotide sequence having 70% or more, 75% or more, 80% or more, 85% or more, 90% or more, 95% or more, 96% or more, 97% or more, 98% or more, and less than 100% homology or identity to the sequence of SEQ ID NO: 6, or may consist of or essentially consist of a nucleotide sequence having 70% or more, 75% or more, 80% or more, 85% or more, 90% or more, 95% or more, 96% or more, 97% or more, 98% or more, and less than 100% homology or identity to the sequence of SEQ ID NO: 6, but is not limited thereto.

In this regard, in the sequence having such homology or identity, a codon encoding the amino acid corresponding to position 182 of SEQ ID NO: 6 may be one of codon encoding alanine.

Further, the polynucleotide of the present disclosure may include a probe that may be prepared from a known gene sequence, for example, a sequence without limitation as long as it is a sequence that may hybridize with a complementary sequence to the entirety or a part of the polynucleotide sequence of the present disclosure under stringent conditions. The "stringent conditions" mean conditions that enable specific hybridization between polynucleotides. These conditions are specifically described in documents (see J. Sambrook et al., Molecular Cloning, A Laboratory Manual, 2nd Edition, Cold Spring Harbor Laboratory press, Cold Spring Harbor, New York, 1989; F. M. Ausubel et al., Current Protocols in Molecular Biology, John Wiley & Sons, Inc., New York, 9.50-9.51, 11.7-11.8). Examples thereof include conditions in which polynucleotides having higher homology or identity, namely, polynucleotides having 70% or more, 75% or more, 80% or more, 85% or more, 90% or more, 95% or more, 96% or more, 97% or more, 98% or more, or 99% or more homology or identity are hybridized with each other while polynucleotides having lower homology or identity are not hybridized with each other, or washing conditions for common Southern hybridization, in which washing is performed once, specifically, two to three times at a salt concentration and temperature equivalent to 60° C., 1×SSC, 0.1% SDS, specifically 60° C., 0.1× SSC, 0.1% SDS, more specifically, 68° C. 0.1× SSC, 0.1% SDS.

Hybridization requires that two nucleic acids have complementary sequences, although mismatches between bases are allowed depending on the stringency of hybridization. The term "complementary" is used to describe the relation between nucleotide bases capable of being hybridized with each other. For example, with regard to DNA, adenine is complementary to thymine and cytosine is complementary to guanine. Therefore, the polynucleotide of the present disclosure may also include substantially similar nucleic acid sequences as well as isolated nucleic acid fragments that are complementary to the entire sequence.

Specifically, a polynucleotide having homology or identity to the polynucleotide of the present disclosure may be detected using hybridization conditions including a hybridization step at a Tm value of 55° C. and the above-described conditions. The Tm value may be 60° C., 63° C., or 65° C., but is not limited thereto, and may be appropriately adjusted by those skilled in the art according to the purpose.

The appropriate stringency to hybridize the polynucleotide depends on the length and degree of complementarity of the polynucleotide, and the variables are well known in the art (e.g., J. Sambrook et al., supra).

Still another aspect of the present disclosure provides a vector including the polynucleotide of the present disclosure. The vector may be an expression vector for expressing the polynucleotide in host cells, but is not limited thereto.

The "vector" of the present disclosure refers to a DNA construct including a polynucleotide sequence encoding a polypeptide of interest operably linked to a suitable expression control region (or expression control sequence) so that the polypeptide of interest may be expressed in a suitable host. The expression control region may include a promoter capable of initiating transcription, any operator sequence for regulating the transcription, a sequence encoding a suitable mRNA ribosome binding site, and a sequence regulating termination of transcription and translation. The vector may be transformed into a suitable host cell and then replicated or function independently of the host genome, or may be integrated into the genome itself.

The vector used in the present disclosure is not particularly limited, but any vector known in the art may be used. Examples of commonly used vectors may include natural or recombinant plasmids, cosmids, viruses, and bacteriophages. For example, pWE15, M13, MBL3, MBL4, IXII, ASHII, APII, t10, t11, Charon4A, Charon21A, or the like may be used as a phage vector or a cosmid vector. pDC system, pBR system, pUC system, pBluescript II system, pGEM system, pTZ system, pCL system, pET system, or the like may be used as a plasmid vector. Specifically, pDC, pDCM2, pACYC177, pACYC184, pCL, pECCG117, pUC19, pBR322, pMW118, pCC1BAC vector or the like may be used.

For example, a polynucleotide encoding a polypeptide of interest may be inserted into a chromosome through a vector for intracellular chromosome insertion. Insertion of the polynucleotide into the chromosome may be performed by any method known in the art, for example, homologous recombination, but is not limited thereto. The vector may further include a selection marker for identifying the chromosome insertion. The selection marker is for selecting the cells transformed with vectors, i.e., for identifying the insertion of a nucleic acid molecule of interest, and markers that confer selectable phenotypes such as drug resistance, auxotrophy, resistance to cytotoxic agents, or expression of surface polypeptides may be used. In an environment treated with a selective agent, only cells expressing the selection marker survive or exhibit other phenotypic traits, and thus transformed cells may be selected.

As used herein, the term "transformation" means that a vector including a polynucleotide encoding a target polypeptide is introduced into a host cell or a microorganism so that the polypeptide encoded by the polynucleotide may be expressed in the host cell. The transformed polynucleotide may be located by being inserted into the chromosome of the host cell or located outside the chromosome as long as it may be expressed in the host cell. Further, the polynucleotide includes DNA and RNA encoding a polypeptide of interest. The polynucleotide may be introduced in any form as long as it may be introduced into a host cell and expressed. For example, the polynucleotide may be introduced into a host cell in the form of an expression cassette, which is a gene construct containing all elements required for self-expression. The expression cassette may usually include a promoter operably linked to the polynucleotide, a transcription termination signal, a ribosome binding site, and a translation termination signal. The expression cassette may be in the form of an expression vector capable of self-replicating. Further, the polynucleotide may be introduced into a host cell in its own form and operably linked to a sequence required for expression in the host cell, but is not limited thereto.

Further, as used herein, the term "operably linked" means that the polynucleotide sequence is functionally linked to a promoter sequence that initiates and mediates transcription of the polynucleotide encoding the variant of interest of the present disclosure.

Still another aspect of the present disclosure provides a microorganism of the genus *Corynebacterium*, the microorganism including the variant of the present disclosure, the polynucleotide of the present disclosure, or the vector of the present disclosure.

The microorganism of the present disclosure may include the polypeptide variant of the present disclosure, the polynucleotide encoding the polypeptide, or the vector including the polynucleotide of the present disclosure.

As used herein, the term "microorganism" or "strain" includes all wild-type microorganisms or naturally or artificially genetically modified microorganisms, and it may be a microorganism in which a specific mechanism is weakened or strengthened due to insertion of a foreign gene or an activity enhancement or inactivation of an endogenous gene, and may be a microorganism including a genetic modification for the production of the polypeptide, protein, or product of interest.

The strain of the present disclosure may be a strain including any one or more of the variant of the present disclosure, the polynucleotide of the present disclosure, and the vector including the polynucleotide of the present disclosure; a strain modified to express the variant of the present disclosure or the polynucleotide of the present disclosure; a strain (e.g., recombinant strain) expressing the variant of the present disclosure or the polynucleotide of the present disclosure; or a strain (e.g., recombinant strain) having the activity of the variant of the present disclosure, but is not limited thereto.

The strain of the present disclosure may be a strain having the branched-chain amino acid-producing ability.

The strain of the present disclosure may be a microorganism naturally having the prephenate dehydratase or branched-chain amino acid-producing ability, or a microorganism prepared by introducing the variant of the present disclosure or the polynucleotide encoding the same (or the vector including the polynucleotide) into the parent strain having no prephenate dehydratase or no branched-chain amino acid-producing ability, and/or by providing the branched-chain amino acid-producing ability for the parent strain, but is not limited thereto.

For example, the strain of the present disclosure may be a cell or microorganism expressing the variant of the present disclosure by transforming with the polynucleotide of the present disclosure or the vector including the polynucleotide encoding the variant of the present disclosure, and with respect to the objects of the present disclosure, the strain of the present disclosure may include all microorganisms capable of producing branched-chain amino acids by including the variant of the present disclosure. For example, the strain of the present disclosure may be a recombinant strain having the enhanced branched-chain amino acid-producing ability, in which the prephenate dehydratase variant is expressed by introducing the polynucleotide encoding the variant of the present disclosure into a natural wild-type or branched-chain amino acid-producing microorganism. The recombinant strain having the enhanced branched-chain amino acid-producing ability may be a microorganism having the enhanced branched-chain amino acid-producing ability, as compared to the natural wild-type or prephenate dehydratase unmodified microorganism (i.e., microorganism expressing the wild-type prephenate dehydratase), but is not limited thereto.

For example, the prephenate dehydratase unmodified microorganism, which is a target strain for comparing whether or not the branched-chain amino acid-producing ability is increased, may be a *Corynebacterium glutamicum* ATCC13032 strain. For another example, the prephenate dehydratase unmodified microorganism, which is a target strain for comparing whether or not the branched-chain amino acid-producing ability is increased, may be CJL-8109, KCCM12739P (CA10-3101), KCCM11201P, but is not limited thereto.

For example, the recombinant strain may have the branched-chain amino acid-producing ability of about 1% or more, and specifically, about 3% or about 5% higher than that of the parent strain before modification or the unmodified microorganism, but is not limited thereto, as long as it has an increased amount of +value, as compared to the production of the parent strain before modification or the unmodified microorganism.

For another example, the recombinant strain may have about 50% or less, specifically, about 30% or less, or about 10% or less of the by-products generated in the branched-chain amino acid production pathway, as compared to the parent strain before modification or the unmodified microorganism, but is not limited thereto.

The term "about" includes all ranges of ±0.5, ±0.4, ±0.3, ±0.2, ±0.1, etc., and includes all numerical values of the ranges equivalent to or similar to the numerical value following the term "about", but is not limited thereto.

As used herein, the term "branched-chain amino acid" refers to an amino acid having a branched alkyl group in the side chain, and includes valine, leucine, and isoleucine. Specifically, in the present disclosure, the branched-chain amino acid may be L-branched-chain amino acid, and the L-branched-chain amino acid may be one or more selected from L-valine, L-leucine, and L-isoleucine, but is not limited thereto.

In the present disclosure, by-products generated in the branched-chain amino acid production pathway refer to substances other than branched-chain amino acids, specifically, aromatic amino acids, and more specifically, one or more selected from L-tyrosine and L-phenylalanine, but are not limited thereto.

As the term "unmodified microorganism" does not exclude strains including mutations that may occur naturally in microorganisms, and may be a wild-type strain or a natural strain itself or may be a strain before the trait is changed by genetic variation due to natural or artificial factors. For example, the unmodified microorganism may be a strain into which the prephenate dehydratase variant of the present disclosure is not introduced or has not yet been introduced. The term "unmodified microorganism" may be used interchangeably with "strain before being modified", "microorganism before being modified", "unvaried strain", "unmodified strain", "unvaried microorganism", or "reference microorganism".

In one embodiment, the microorganism of the present disclosure may be *Corynebacterium glutamicum, Corynebacterium stationis, Corynebacterium crudilactis, Corynebacterium deserti, Corynebacterium efficiens, Corynebacterium callunae, Corynebacterium singulare, Corynebacterium halotolerans, Corynebacterium striatum, Corynebacterium ammoniagenes, Corynebacterium pollutisoli. Corynebacterium imitans, Corynebacterium testudinoris,* or *Corynebacterium flavescens.*

The microorganism of the present disclosure may further include a variation to increase the branched-chain amino acid-producing ability.

In one embodiment, the microorganism of the present disclosure may include a modification of the activity of one or more of isopropylmalate synthase, homoserine dehydrogenase, threonine dehydratase, branched-chain amino acid aminotransferase, and citrate synthase.

In one embodiment, the microorganism of the present disclosure may be a microorganism, in which the activity of one or more of isopropylmalate synthase, homoserine dehydrogenase, branched-chain amino acid aminotransferase, and threonine dehydratase is additionally enhanced.

However, the microorganism is not limited to the above description, and those skilled in the art may appropriately select additional modifications included in the microorganism, according to the branched-chain amino acid to be produced.

As used herein, the term "enhancement" of polypeptide activity means that the activity of a polypeptide is increased as compared to the intrinsic activity. The enhancement may be used interchangeably with terms such as activation, up-regulation, overexpression, increase, etc. Here, activation, enhancement, up-regulation, overexpression, and increase may include both exhibiting activity that was not originally possessed and exhibiting improved activity, as compared to the intrinsic activity or activity before modification. The "intrinsic activity" means activity of a specific polypeptide originally possessed by a parent strain before change of the trait or an unmodified microorganism when the trait is changed by genetic variation due to natural or artificial factors. This may be used interchangeably with "activity before modification". The fact that the activity of a polypeptide is "enhanced", "up-regulated", "overexpressed", or "increased", as compared to the intrinsic activity, means that the activity of a polypeptide is improved, as compared to the activity and/or concentration (expression level) of a specific polypeptide originally possessed by a parent strain before change of the trait or an unmodified microorganism.

The enhancement may be achieved through the introduction of a foreign polypeptide or the enhancement of intrinsic activity and/or concentration (expression level) of the polypeptide. The activity enhancement of a polypeptide may be confirmed by an increase in the degree of activity and the expression level of the corresponding polypeptide or in the amount of a product produced from the corresponding polypeptide.

For the activity enhancement of the polypeptide, various methods well known in the art may be applied, and the method is not limited as long as the activity of the polypeptide of interest may be enhanced, as compared to that of the microorganism before being modified. Specifically, genetic engineering and/or protein engineering well known to those skilled in the art, which are routine methods of molecular biology, may be used, but the method is not limited thereto (e.g., Sitnicka et al. Functional Analysis of Genes. Advances in Cell Biology. 2010, Vol. 2. 1-16, Sambrook et al. Molecular Cloning 2012, etc.).

Specifically, the enhancement of the polypeptide of the present disclosure may be:

1) increase in the intracellular copy number of the polynucleotide encoding the polypeptide;

2) replacement of a gene expression regulatory region on a chromosome encoding the polypeptide with a sequence exhibiting strong activity;

3) modification of a start codon of a gene transcript encoding the polypeptide or a base sequence encoding a 5'-UTR region;

4) modification of the amino acid sequence of the polypeptide to enhance the activity of the polypeptide;

5) modification of the polynucleotide sequence encoding the polypeptide to enhance the activity of the polypeptide (e.g., modification of the polynucleotide sequence of the polypeptide gene to encode the polypeptide that has been modified to enhance the activity of the polypeptide);

6) introduction of a foreign polypeptide exhibiting the activity of the polypeptide or a foreign polynucleotide encoding the polypeptide;

7) codon optimization of a polynucleotide encoding the polypeptide;

8) analysis of the tertiary structure of the polypeptide to select the exposed site and to perform modification or chemical modification of the exposed site; or 9) a combination of two or more selected from 1) to 8), but is not particularly limited thereto.

More specifically, 1) the increase in the intracellular copy number of the polynucleotide encoding the polypeptide may be performed by introducing a vector, which replicates and functions irrespective of a host cell and is operably linked to the polynucleotide encoding the corresponding polypeptide, into a host cell. Alternatively, the increase may be achieved by the introduction of one copy or two or more copies of the polynucleotide encoding the corresponding polypeptide into a chromosome of a host cell. The introduction into the chromosome may be performed by introducing a vector capable of inserting the polynucleotide into a chromosome of a host cell into the host cell, but is not limited thereto. The vector is as described above.

2) The replacement of a gene expression control region (or expression control sequence) on a chromosome encoding a polypeptide with a sequence exhibiting strong activity may be, for example, occurrence of variation in a sequence due to deletion, insertion, non-conservative or conservative substitution, a combination thereof, or replacement with a sequence exhibiting stronger activity so that the activity of the expression control region is further enhanced. The expression control region is not particularly limited thereto, but may include a promoter, an operator sequence, a sequence encoding a ribosome binding site, a sequence controlling the termination of transcription and translation, and the like. For example, the replacement may be to replace the original promoter with a strong promoter, but is not limited thereto.

Examples of known strong promoters include cj1 to cj7 promoters (U.S. Pat. No. 7,662,943 B2), lac promoter, trp promoter, trc promoter, tac promoter, lambda phage PR promoter, PL promoter, tet promoter, gapA promoter, SPL7 promoter, SPL13 (sm3) promoter (U.S. Pat. No. 10,584,338 B2), O2 promoter (U.S. Pat. No. 10,273,491 B2), tkt promoter, yccA promoter, etc., but are not limited thereto.

3) The modification of a start codon of the gene transcript encoding the polypeptide or a base sequence encoding a 5'-UTR region may be, for example, substitution with a base sequence encoding another start codon having a higher polypeptide expression rate, as compared to an endogenous start codon, but is not limited thereto.

4) and 5) The modification of the amino acid sequence or polynucleotide sequence may be occurrence of variation in the sequence due to deletion, insertion, nonconservative or conservative substitution of an amino acid sequence of the polypeptide or a polynucleotide sequence encoding the polypeptide, or a combination thereof, or replacement with an amino acid sequence or polynucleotide sequence modified to exhibit stronger activity or an amino acid sequence or polynucleotide sequence modified to be more active so that the activity of the polypeptide is enhanced, but is not limited thereto. The replacement may be specifically performed by inserting a polynucleotide into a chromosome by homologous recombination, but is not limited thereto. The vector used here may further include a selection marker for the confirmation of chromosome insertion. The selection marker is as described above.

6) The introduction of a foreign polynucleotide exhibiting the activity of the polypeptide may be the introduction of a foreign polynucleotide encoding a polypeptide exhibiting activity the same as or similar to that of the polypeptide into a host cell. The foreign polynucleotide is not limited in its origin or sequence as long as it exhibits activity the same as or similar to that of the polypeptide. The method used in the introduction may be performed by appropriately selecting a known transformation method by those skilled in the art. As the introduced polynucleotide is expressed in a host cell, a polypeptide may be produced, and the activity thereof may be increased.

7) The codon optimization of the polynucleotide encoding the polypeptide may be codon optimization of an endogenous polynucleotide so as to increase transcription or translation in a host cell or codon optimization of a foreign polynucleotide so as to perform optimized transcription and translation in a host cell.

8) The analysis of the tertiary structure of the polypeptide to select the exposed site and to perform modification or chemical modification of the exposed site may be, for example, to determine a template protein candidate according to the degree of similarity of the sequence by comparing the sequence information of a polypeptide to be analyzed with a database storing the sequence information of known proteins, to confirm the structure based on this, and to select and to modify or chemically modify the exposed portion to be modified or chemically modified.

Such enhancement of the polypeptide activity may be an increase in the activity or concentration (expression level) of the corresponding polypeptide, based on the activity or concentration of the polypeptide expressed in a wild-type or a microbial strain before being modified, or an increase in the amount of a product produced from the corresponding polypeptide, but is not limited thereto.

In the microorganism of the present disclosure, partial or entire modification of a polynucleotide may be induced by (a) homologous recombination using a vector for chromosome insertion in the microorganism or genome editing using engineered nuclease (e.g., CRISPR-Cas9) and/or (b) treatment with light such as ultraviolet rays and radiation and/or chemicals, but is not limited thereto. A method of modifying a part or the entirety of the gene may include a method using DNA recombination technology. For example, by introducing a nucleotide sequence or vector containing a nucleotide sequence homologous to the gene of interest into the microorganism to cause homologous recombination, a part or the entirety of the gene may be deleted. The introduced nucleotide sequence or vector may include a dominant selection marker, but is not limited thereto.

As used herein, the term "weakening" of activity of a polypeptide is a concept including both cases where the activity is decreased, as compared to the endogenous activity, or the activity is absent. The weakening may be used interchangeably with terms such as inactivation, deficiency, down-regulation, decrease, reduce, attenuation, etc.

The weakening may also include a case where the activity of the polypeptide itself is decreased or eliminated due to variation of the polynucleotide encoding the polypeptide, etc., as compared to the activity of the polypeptide originally possessed by the microorganism, a case where the overall polypeptide activity level and/or concentration (expression level) in the cell is low due to inhibition of the expression of the gene of the polynucleotide encoding the polypeptide or by inhibition of translation into the polypeptide, as compared to that of the natural strain, a case where the polynucleotide is not expressed at all, and/or a case where the polypeptide activity is absent even when the polynucleotide is expressed. The "endogenous activity" means the activity of a specific polypeptide originally possessed by the parent strain before change of the trait or a wild-type or unmodified microorganism when the trait is changed by genetic variation due to natural or artificial factors. The endogenous activity may be used interchangeably with "activity before modification". The fact that the activity of a polypeptide is "inactivated, deficient, decreased, down-regulated, reduced, or attenuated" as compared to the endogenous activity means that the activity of a polypeptide is lowered, as compared to the activity of a specific polypeptide originally possessed by the parent strain before change of the trait or the unmodified microorganism.

Such weakening of the activity of a polypeptide may be performed by any method known in the art, but the method is not limited thereto, and the weakening may be achieved by applying various methods well known in the art (e.g., Nakashima N et al., Bacterial cellular engineering by genome editing and gene silencing. Int J Mol Sci. 2014; 15 (2): 2773-2793, Sambrook et al. Molecular Cloning 2012, etc.).

Specifically, the weakening of the polypeptide of the present disclosure may be:

1) deletion of the entirety or a part of the gene encoding the polypeptide;

2) modification of an expression regulatory region (or expression regulatory sequence) to decrease expression of the gene encoding the polypeptide;

3) modification of an amino acid sequence constituting the polypeptide to eliminate or weaken the activity of the polypeptide (e.g., deletion/substitution/addition of one or more amino acids in the amino acid sequence);

4) modification of a gene sequence encoding the polypeptide to eliminate or weaken the activity of the polypeptide (e.g., deletion/substitution/addition of one or more nucleic acid bases in a nucleic acid base sequence of the polypeptide gene to encode the polypeptide that has been modified to eliminate or weaken the activity of the polypeptide);

5) modification of a start codon of a gene transcript encoding the polypeptide or a base sequence encoding a 5'-UTR region;

6) introduction of an antisense oligonucleotide (e.g., antisense RNA) that complementarily binds to the transcript of the gene encoding the polypeptide;

7) addition of a sequence complementary to a Shine-Dalgamo sequence in front of the Shine-Dalgamo sequence of the gene encoding the polypeptide in order to form a secondary structure to which ribosome cannot be attached;

8) addition of a promoter to be transcribed in the opposite direction to the 3' end of the open reading frame (ORF) of the gene sequence encoding the polypeptide (reverse transcription engineering, RTE); or 9) a combination of two or more selected from 1) to 8), but is not particularly limited thereto.

For example, 1) the deletion of a part or the entirety of the gene encoding the polypeptide may be removal of the entire polynucleotide encoding the intrinsic polypeptide of interest in the chromosome, replacement with a polynucleotide in which some nucleotides are deleted, or replacement with a marker gene.

Further, 2) the modification of the expression regulatory region (or expression regulatory sequence) may be occurrence of variation in the expression regulatory region (or expression regulatory sequence) due to deletion, insertion, non-conservative or conservative substitution, or a combination thereof, or replacement with a sequence exhibiting weaker activity. The expression regulatory region includes a promoter, an operator sequence, a sequence encoding a ribosome binding site, and a sequence regulating the termination of transcription and translation, but is not limited thereto.

Further, 3) the modification of a start codon of a gene transcript encoding the polypeptide or a base sequence encoding a 5'-UTR region may be, for example, substitution with a base sequence encoding another start codon having a lower polypeptide expression rate, as compared to an intrinsic start codon, but is not limited thereto.

Further, 4) and 5) the modification of the amino acid sequence or polynucleotide sequence may be occurrence of variation in the sequence due to deletion, insertion, or non-conservative or conservative substitution of the amino acid sequence of the polypeptide or the polynucleotide sequence encoding the polypeptide or a combination thereof, or replacement with an amino acid sequence or a polynucleotide sequence modified to exhibit weaker activity or an amino acid sequence or a polynucleotide sequence modified to be inactive so that the activity of the polypeptide is weakened, but is not limited thereto. For example, expression of the gene may be inhibited or weakened by introducing variation into the polynucleotide sequence and forming a stop codon, but is not limited thereto.

Further, 6) the introduction of an antisense oligonucleotide (e.g., antisense RNA) that complementarily binds to the transcript of the gene encoding the polypeptide, may refer to documents, for example. [Weintraub, H. et al., Antisense-RNA as a molecular tool for genetic analysis, Reviews-Trends in Genetics, Vol. 1 (1) 1986].

Further, 7) the addition of a sequence complementary to a Shine-Dalgarno sequence in front of the Shine-Dalgarno sequence of the gene encoding the polypeptide in order to form a secondary structure to which ribosome cannot be attached may be to make mRNA translation impossible or to slow down the mRNA translation rate.

Further, 8) the addition of a promoter to be transcribed in the opposite direction to the 3' end of the open reading frame (ORF) of the gene sequence encoding the polypeptide (reverse transcription engineering, RTE) may be to weaken the activity by making an antisense nucleotide complementary to the transcript of the gene encoding the polypeptide.

In the microorganism of the present disclosure, the variant, polynucleotide, vector, and branched-chain amino acids are as described in other aspects.

Still another aspect of the present disclosure provides a method of producing branched-chain amino acids, the method including a step of culturing, in a medium, the microorganism of the genus *Corynebacterium* of the present disclosure.

As used herein, the term "culture" means growing the microorganism of the genus *Corynebacterium* of the present disclosure under appropriately controlled environmental conditions. The culture process of the present disclosure may be performed according to suitable medium and culture conditions known in the art. Such a culture process may be easily adjusted and used by those skilled in the art according to the selected strain. Specifically, the culture may be a batch type, continuous type, and/or fed-batch type, but is not limited thereto.

As used herein, the term "medium" means a mixed substance containing nutrients required to culture the microorganism of the genus *Corynebacterium* of the present disclosure as a main component, and the medium supplies nutrients and growth factors, including water, which are indispensable for survival and development. Specifically, as the medium and other culture conditions used for culture of the microorganism of the genus *Corynebacterium* of the present disclosure, any one may be used without particular limitation as long as it is a medium used for common culture of microorganisms. The microorganism of the genus *Corynebacterium* of the present disclosure may be cultured in a common medium containing proper carbon sources, nitrogen sources, phosphorus sources, inorganic compounds, amino acids and/or vitamins, etc., while controlling the temperature, pH, etc. under aerobic conditions.

Specifically, the culture medium for the microorganism of the genus *Corynebacterium* may be found in the document ["Manual of Methods for General Bacteriology" by the American Society for Bacteriology (Washington D.C., USA, 1981)].

In the present disclosure, the carbon sources include carbohydrates such as glucose, saccharose, lactose, fructose, sucrose, maltose, etc.; sugar alcohols such as mannitol, sorbitol, etc., organic acids such as pyruvic acid, lactic acid, citric acid, etc.; amino acids such as glutamic acid, methionine, lysine, etc.; and the like. Natural organic nutrients such as starch hydrolysate, molasses, blackstrap molasses, rice bran, cassava, sugarcane residue, and corn steep liquor may be used. Specifically, carbohydrates such as glucose and sterilized pretreated molasses (i.e., molasses converted to reducing sugar) may be used, and appropriate amounts of other carbon sources may be used in various manners without limitation. These carbon sources may be used alone or in combination of two or more thereof, but are not limited thereto.

As the nitrogen sources, inorganic nitrogen sources such as ammonia, ammonium sulfate, ammonium chloride, ammonium acetate, ammonium phosphate, ammonium carbonate, ammonium nitrate, etc.; and organic nitrogen sources such as amino acids such as glutamic acid, methionine, glutamine, etc., peptone. NZ-amine, meat extract, yeast extract, malt extract, corn steep liquor, casein hydrolysate, fish or decomposition products thereof, and skim soybean cake or decomposition products thereof, etc. may be used. These nitrogen sources may be used alone or in combination of two or more thereof, but are not limited thereto.

The phosphorus sources may include monopotassium phosphate, dipotassium phosphate, or sodium-containing salts corresponding thereto. As the inorganic compounds, sodium chloride, calcium chloride, iron chloride, magnesium sulfate, iron sulfate, manganese sulfate, calcium carbonate, etc. may be used. In addition to these compounds, amino acids, vitamins and/or suitable precursors, etc. may be included. These components or precursors may be added to the medium batchwise or continuously, but is not limited thereto.

Further, during the culture of the microorganism of the genus *Corynebacterium* of the present disclosure, pH of the medium may be adjusted by adding compounds such as ammonium hydroxide, potassium hydroxide, ammonia, phosphoric acid, or sulfuric acid to the medium in a proper manner. During the culture, foaming may be suppressed by using an antifoaming agent such as fatty acid polyglycol ester. Oxygen or oxygen-containing gas may be injected into the medium in order to maintain the aerobic state of the medium, or gas may not be injected or nitrogen, hydrogen, or carbon dioxide gas may be injected in order to maintain the anaerobic and microaerobic states, but is not limited thereto.

In the culture of the present disclosure, the culture temperature may be maintained at 20° C. to 45° C., specifically, at 25° C. to 40° C., and the microorganism may be cultured for about 10 hours to about 160 hours, but are not limited thereto.

Branched-chain amino acids produced through the culture of the present disclosure may be secreted into the medium or may remain in the cells.

The method of producing branched-chain amino acids of the present disclosure may further include a step of preparing the microorganism of the genus *Corynebacterium* of the present disclosure, a step of preparing a medium for culture of the strain, or a combination of these steps (in any order), for example, prior to the culture step.

The method of producing branched-chain amino acids of the present disclosure may further include a step of recovering branched-chain amino acids from the medium according to the culture (the medium subjected to the culture) or from the microorganism of the genus *Corynebacterium* of the present disclosure. The recovery step may be further included after the culture step.

The recovery may be to collect branched-chain amino acids of interest by way of a suitable method known in the art according to the method of culturing the microorganism of the present disclosure, for example, a batch, continuous, or fed-batch culture method. For example, centrifugation, filtration, treatment with a crystallized protein precipitant (salting out), extraction, ultrasonic disintegration, ultrafiltration, dialysis, various forms of chromatography such as molecular sieve chromatography (gel filtration), adsorption chromatography, ion-exchange chromatography, and affinity chromatography, HPLC, or a combination thereof may be used. The branched chain amino acids of interest may be recovered from the medium or microorganism by way of a suitable method known in the art.

Further, the method of producing branched-chain amino acids of the present disclosure may further include a purification step. The purification may be performed by way of a suitable method known in the art. For example, when the method of producing branched-chain amino acids of the present disclosure includes both the recovery step and the purification step, the recovery step and the purification step may be performed discontinuously (or continuously) regardless of the order, or may be performed simultaneously or by being combined into one step, but is not limited thereto.

In the method of the present disclosure, the variant, polynucleotide, vector, microorganism and the like are as described in other aspects.

Still another aspect of the present disclosure provides a composition for producing branched-chain amino acids, the composition including the variant of the present disclosure, the polynucleotide encoding the variant, the vector including the polynucleotide, or the microorganism of the genus *Corynebacterium* including the polynucleotide of the present disclosure; a medium in which the microorganism has been cultured; or a combination of two or more thereof.

The composition of the present disclosure may further include arbitrary suitable excipients to be commonly used in compositions for producing branched-chain amino acids. Such excipients may be, for example, a preservative, a wetting agent, a dispersing agent, a suspending agent, a buffering agent, a stabilizer, or an isotonic agent, but are not limited thereto.

In the composition of the present disclosure, the variant, polynucleotide, vector, strain, medium, branched chain amino acids, and the like are as described in other aspects.

Still another aspect of the present disclosure provides use of the microorganism including one or more of the prephenate dehydratase variant of the present disclosure; the polynucleotide encoding the prephenate dehydratase variant; and the vector including the polynucleotide, in the production of branched-chain amino acids.

In the use of the present disclosure, the variant, polynucleotide, vector, microorganism and the like are as described in other aspects.

Hereinafter, the present disclosure will be described in more detail with reference to Examples and Experimental Examples. However, these Examples and Experimental Examples are only for illustrating the present disclosure, and the scope of the present disclosure is not intended to be limited by these Examples and Experimental Examples.

Example 1: Discovery of pheA Variation

Example 1-1. Construction of Vector Including pheA

To construct a pheA mutant library having a prephenate dehydratase activity, a recombinant vector including pheA was first constructed. To amplify pheA gene (SEQ ID NO: 2) encoding pheA protein (SEQ ID NO: 1, Uniprot ID: P10341) derived from the wild-type *Corynebacterium glutamicum*, PCR was performed using the chromosome of the wild-type strain *Corynebacterium glutamicum* ATCC13032 as a template and primers of SEQ ID NOS: 3 and 4 under conditions of 25 cycles of denaturation at 94° C. for 1 minute, annealing at 58° C. for 30 seconds, polymerization at 72° C. for 1 minute with Pfu DNA polymerase. The specific sequences of the used primers are listed in Table 1. The amplification product was cloned into *E. coli* vector pCR2.1 using a TOPO Cloning Kit (Invitrogen) to obtain 'pCR-pheA'.

TABLE 1

| SEQ ID NO. | Sequence(5'->3') |
| --- | --- |
| SEQ ID NO: 3 | TTGAGGTCCTTGGCTGG |
| SEQ ID NO: 4 | CGCAACACGATGGAGCTG |

Example 1-2. Construction of pheA Mutant Library

Based on the vector prepared in Example 1-1, a pheA mutant library was constructed using an error-prone PCR kit (clontech Diversify® PCR Random Mutagenesis Kit). A PCR reaction was performed using SEQ ID NO: 3 and SEQ ID NO: 4 as primers under conditions where 0 to 3 mutations could occur per 1000 bp. In detail, the PCR reaction was performed by pre-heating at 94° C. for 30 seconds, followed by 25 cycles of at 94° C. for 30 seconds, and at 68° C. for 1 minute 30 seconds. The PCR product thus obtained was used as a megaprimer (50 to 125 ng), followed by 25 cycles of at 95° C. for 50 seconds and at 60° C. for 50 seconds, and at 68° C. for 12 minutes, and then treated with Dpnl, and transformed into *E. coli* DH5a by a heat shock method and spread on LB solid medium containing kanamycin (25 mg/L). 20 types of transformed colonies were selected, and plasmids were obtained, followed by sequence analysis. As a result, it was confirmed that variations were introduced at different positions with a frequency of 2 mutations/kb. About 20,000 transformed *E. coli* colonies were taken and plasmids were extracted, which was named 'pTOPO-pheA-library'.

Example 2: Evaluation of Constructed Library and Selection of Variant

Example 2-1. Selection of Mutant Strains with Increased or Decreased Production of L-Leucine and L-Phenylalanine The pTOPO-pheA-library prepared in Example 1-2 was transformed into the wild-type *Corynebacterium glutamicum* ATCC13032 by electroporation, and then plated on a nutrient medium (Table 2) containing 25 mg/L kanamycin. 10,000 colonies of the strain into which the mutant gene was inserted were selected. Each of the selected colonies was named from ATCC13032/pTOPO_pheA (mt) 1 to ATCC13032/pTOPO_pheA (mt) 10,000.

To identify colonies showing the increased production of L-leucine and the increased or decreased production of L-phenylalanine which is an aromatic amino acid, among the obtained 10,000 colonies, the fermentation titer was evaluated for each colony in the following manner.

TABLE 2

| Type of medium | Ingredient |
|---|---|
| Production medium | 100 g of glucose, 40 g of $(NH_4)_2SO_4$, 2.5 g of soy protein, 5 g of corn steep solids, 3 g of urea, 1 g of $KH_2PO_4$, 0.5 g of $MgSO_4 \cdot 7H_2O$, 100 µg of biotin, 1,000 µg of thiamine hydrochloride, 2000 µg of calcium-pantothenic acid, 3,000 µg of nicotinamide, 30 g of $CaCO_3$; (Based on 1 liter of distilled water), pH 7.0 |
| Nutrient medium | 10 g of glucose, 5 g of beef extract, 10 g of polypeptone, 2.5 g of sodium chloride, 5 g of yeast extract, 20 g of agar, 2 g of urea (based on 1 liter of distilled water) |

Each colony was inoculated into a 250 ml corner-baffle flask containing 25 g/mL kanamycin in 25 ml of autoclaved production medium (Table 2) using a platinum loop, and then cultured at 30° C. for 60 hours under shaking at 200 rpm. After completion of the culture, L-leucine and L-phenylalanine among aromatic amino acids were measured by a method of using high-performance liquid chromatography (HPLC. SHIMAZDU LC20A).

Among the obtained 10,000 colonies, one type of a strain (ATCC13032/pTOPO_pheA (mt) 3891) with the most improved L-leucine-producing ability and reduced L-phenylalanine production, as compared to the wild-type *Corynebacterium glutamicum* strain (ATCC13032), was selected. The concentrations of L-leucine (Leu) and L-phenylalanine (Phe) produced in the selected strain are shown in Table 3 below.

TABLE 3

| Strain name | Leu (g/L) | Phe (g/L) |
|---|---|---|
| ATCC13032 | 0.87 | 1.85 |
| ATCC13032/pTOPO_pheA(mt)3891 | 1.25 | 0.26 |

As shown in Table 3, it was confirmed that *Corynebacterium glutamicum* ATCC13032/pTOPO_pheA (mt) 3891 with variations in the pheA gene showed about 1.4-fold improvement in the L-leucine production and about 7-fold reduction in the L-phenylalanine production, as compared to the parent strain.

Example 2-2. Identification of Variations in Strains with Increased or Decreased Production of L-Leucine and L-Phenylalanine In order to identify the pheA gene variations of the selected mutant strain ATCC13032/pTOPO_pheA (mt) 3891, DNA of each mutant strain was used as a template and primers of SEQ ID NO: 3 and SEQ ID NO: 4 described in Table 1 were used to perform PCR under conditions of denaturation at 94° C. for 5 minutes, followed by 30 cycles of at 94° C. for 30 seconds, at 55° C. for 30 seconds, and at 72° C. for 1 minute and 30 seconds, and then at 72° C. for 5 minutes. Then, DNA sequencing was performed.

As a result of sequencing, it was confirmed that the ATCC13032/pTOPO_pheA (mt) 3891 strain had a substitution of GCG for CGC which are nucleotides at positions 544 to 546 of the pheA gene, indicating that it encodes a variant (hereinafter referred to as R182A), in which alanine is substituted for arginine which is an amino acid at position 182 of the pheA protein. The amino acid sequence of pheA variant (R182A) and the base sequence of pheA variant encoding the same are as in SEQ ID NOS: 5 and 6.

Therefore, in the following Examples, it was tried to confirm whether the variation (R182A) affects the production of L-leucine and aromatic amino acid by the microorganism of the genus *Corynebacterium*.

Example 3: Examination of L-Leucine- and L-Phenylalanine-Producing Ability of Selected Mutant Strains Example 3-1. Construction of Insertion Vector Including pheA Variation In order to introduce the variation selected in Example 2 into the strain, an insertion vector was intended to be constructed. The vector for introducing the pheA (R182A) variation was constructed using a site directed mutagenesis method. In order to generate the R182A variation using the chromosome of the wild-type *Corynebacterium glutamicum* as a template, a primer pair of SEQ ID NOS: 7 and 8 and a primer pair of SEQ ID NOS: 9 and 10 were used to perform PCR. In detail, PCR was performed under conditions of denaturation at 94° C. for 5 minutes, followed by 30 cycles of at 94° C. for 30 seconds, at 55° C. for 30 seconds, and at 72° C. for 1 minute 30 seconds, and then at 72° C. for 5 minutes. The specific sequences of the used primers are listed in Table 4.

TABLE 4

| SEQ ID NO. | Sequence(5'->3') |
|---|---|
| SEQ ID NO: 7 | GTGAATTCGAGCTCGGTAC CCGTGGCATGGATGAAAAG |
| SEQ ID NO: 8 | TTGGACAGCAACGAAGCGG GTCgcGGCGCCACGGAC |
| SEQ ID NO: 9 | GTCGCCGACGTCCGTGGCG CCgcgACCCGCTTCGTTG |
| SEQ ID NO: 10 | GGTCGACTCTAGAGGATCC CCGTGGCTGTCCATGATTC |

The resulting PCR product was cloned into a linear pDCM2 vector (Korean Patent Publication No. KR 10-2020-0136813 A) digested with SmaI restriction enzyme through fusion of the homologous sequence of the terminal 15 bases between the DNA fragments using In-Fusion enzyme to construct a vector 'pDCM2-pheA (R182A)' in which the amino acid at position 182 of pheA was substituted with alanine.

Example 3-2. Introduction of Variant into ATCC13032 Strain and Evaluation

The pDCM2-pheA (R182A) vector constructed in Example 3-1 was transformed into ATCC13032 by electroporation, and the strains in which the vector was inserted on the chromosome by recombination of the homologous sequence were selected on a medium containing 25 mg/L kanamycin. The selected primary strains were again subjected to secondary crossover, and strains into which the target gene variation was introduced were selected. Finally, whether or not the pheA gene variation was introduced into the transformed strain was confirmed by performing PCR using primers of SEQ ID NOS: 3 and 4, and then analyzing the nucleotide sequence, thereby identifying introduction of the variation into the strain. A total of 3 types of strains were prepared, and named ATCC13032_pheA_R182A.

In order to evaluate the L-leucine- and aromatic amino acid-producing ability of a total of 3 strains thus prepared, a flask fermentation titer was evaluated. Each one platinum loop of the parent strain *Corynebacterium glutamicum* ATCC13032 and the prepared ATCC13032_pheA_R182A was inoculated into a 250 ml corner-baffle flask containing 25 ml of a production medium, and then cultured at 30° C. for 60 hours under shaking at 200 rpm to produce L-leucine. After completion of the culture, L-leucine, L-tyrosine, and L-phenylalanine productions were measured by HPLC. The concentration of leucine in the culture medium of each tested strain is shown in Table 5 below.

TABLE 5

| Strain name | Leu (g/L) | Phe (g/L) |
|---|---|---|
| ATCC13032 | 0.87 | 1.85 |
| ATCC13032 _pheA_R182A | 1.27 | 0.22 |

As shown in Table 5, ATCC13032_pheA_R182A showed about 1.5-fold improvement in the L-leucine yield, as compared to the parent strain *Corynebacterium glutamicum* ATCC13032. ATCC13032_pheA_R182A showed about 8-fold reduction in the L-phenylalanine production.

Example 4: Examination of Leucine- and Phenylalanine-Producing Ability of Selected pheA Variation in Leucine-Producing Strain The wild-type strain of the genus *Corynebacterium* produces only trace amounts of leucine even though it produces leucine. Accordingly, a leucine-producing strain derived from ATCC13032 was prepared, and the selected variations were introduced to perform an experiment for examining the leucine- and phenylalanine-producing ability. The detailed experimental method is as follows.

Example 4-1. Preparation of L-Leucine-Producing CJL-8109 Strain

As strains for producing high concentrations of L-leucine, the ATCC13032-derived strains were prepared, each including (1) a variation (R558H), in which histidine was substituted for arginine which is an amino acid at position 558 of LeuA protein by substituting A for G which is a nucleotide at position 1673 of leuA gene, (2) a variation (G561D), in which aspartic acid was substituted for glycine which is an amino acid at position 561 of LeuA protein by substituting AT for GC which are nucleotides at positions 1682 and 1683 of leuA gene, or (3) a variation (P247C), in which cysteine was substituted for proline which is an amino acid at position 247 of LeuA protein by substituting TG for CC which are nucleotides at positions 739 and 740 of leuA gene.

In detail, pDCM2-leuA (P247C, R558H, G561D) vector including the leuA gene variations was transformed into *Corynebacterium glutamicum* ATCC13032 by electroporation, and strains in which the vector was inserted on the chromosome by recombination of homologous sequence were selected in a medium containing 25 mg/L kanamycin. The selected primary strains were again subjected to secondary crossover, and strains into which the leuA gene variation was introduced were selected. Finally, whether or not the variation was introduced into the transformed strain was confirmed by performing PCR (at 94° C. for 5 minutes, followed by 30 cycles of at 94° C. for 30 seconds/at 55° C. for 30 seconds/at 72"° C. for 90 seconds, and at 72° C. for 5 minutes) using primers of SEQ ID NOS: 11 and 12 of Table 6, and then analyzing the nucleotide sequence, thereby identifying introduction of P247C, R558H, G561D variations. ATCC13032_leuA_(P247C, R558H, G561D) strain transformed with the pDCM2-leuA (P247C, R558H, G561D) vector was named 'CJL-8105'.

TABLE 6

| SEQ ID NO: | Sequence(5'->3') |
|---|---|
| SEQ ID NO: 11 | TATGCTTCACCACATGACTTC |
| SEQ ID NO: 12 | AAATCATTTGAGAAAACTCGAGG |

To increase the L-leucine productivity in the prepared CJL-8105 strain, a strain into which ilvE variant (V156A) encoding branched-chain amino acid aminotransferase was introduced was prepared (Korean Patent No. KR 10-2143964 B1). In detail, the pDCM2-ilvE (V156A) vector including the ilvE gene variation was transformed into *Corynebacterium glutamicum* CJL-8105 by electroporation, and strains in which the vector was inserted on the chromosome by recombination of homologous sequence were selected in a medium containing 25 mg/L kanamycin. The selected primary strains were again subjected to secondary crossover, and strains into which the ilvE gene variation was introduced were selected. Finally, whether or not the variation was introduced into the transformed strain was confirmed by performing PCR (at 94° C. for 5 minutes, 30 cycles of at 94° C. 30 seconds/at 55° C. 30 seconds/at 72° C. 90 seconds, followed by at 72° C. for 5 minutes) using primers of SEQ ID NOS: 13 and 14 of Table 7 below, and then analyzing the nucleotide sequence, thereby identifying introduction of V156A variation. The strain transformed with the pDCM2-ilvE (V156A) vector was named 'CJL-8108'

TABLE 7

| SEQ ID NO: | Sequence(5'->3') |
|---|---|
| 13 | GTCACCCGATCGTCTGAAG |
| 14 | GTCTTAAAACCGGTTGAT |

To increase the L-leucine productivity in the prepared CJL-8108 strain, a strain into which gitA variant (M312I; SEQ ID NO: 25) with weakened citrate synthase activity was introduced was prepared. In detail, pDCM2-gitA (M312I) vector including the gitA gene variation was transformed into *Corynebacterium glutamicum* CJL-8108 by electroporation, and strains in which the vector was inserted on the chromosome by recombination of homologous sequence were selected in a medium containing 25 mg/L kanamycin. The selected primary strains were again subjected to secondary crossover, and strains into which the gitA gene variation was introduced were selected. Finally, whether or not the variation was introduced into the transformed strain was confirmed by performing PCR (at 94° C. for 5 minutes, 30 cycles of at 94° C. 30 seconds/at 55° C. 30 seconds/at 72° C. 90 seconds, followed by 72° C. for 5 minutes) using primers of SEQ ID NOS: 15 and 16 of Table 8, and then analyzing the nucleotide sequence, thereby identifying introduction of M312I variation. The strain transformed with the pDCM2-gitA (M312I) vector was named 'CJL-8109'.

TABLE 8

| SEQ ID NO: | Sequence(5'->3') |
|---|---|
| 15 | CAATGCTGGCTGCGTACGC |
| 16 | CTCCTCGCGAGGAACCAACT |

Example 4-2. Introduction of pheA Variant into CJL-8109 Strain and Evaluation The L-leucine-producing strain CJL-8109 was transformed with the pDCM2-pheA (R182A) vector prepared in Example 3-1, and the strains, in which the vector was inserted on the chromosome by recombination of the homologous sequence, were selected in a medium containing 25 mg/L kanamycin. The selected primary strains were again subjected to secondary crossover, and strains into which the target gene variation was introduced were selected. Finally, whether or not the pheA gene variation was introduced into the transformed strain was confirmed by performing PCR using primers of SEQ ID NO: 3 and SEQ ID NO: 4, and then analyzing the nucleotide sequence, thereby identifying that the pheA variation was introduced into the strain. The prepared CJL8109_pheA_R182A was named CA13-8116, and deposited at the Korean Culture Center of Microorganisms (KCCM), an international depository authority under the Budapest Treaty, on Jan. 22, 2021, and assigned Accession No. KCCM12943P.

The leucine-producing ability of the prepared CA13-8116 and ATCC13032. CJL-8109 strains was evaluated. In the same manner as in Example 2, flask culture was performed, and after completion of the culture, the leucine production was measured by a method of using HPLC, and the culture results are as in Table 9 below.

TABLE 9

| Strain name | Leu (g/L) | Phe (g/L) |
|---|---|---|
| ATCC13032 | 0.87 | 1.87 |
| ATCC13032_leuA_(P247C, R558H, G561D)_ilvE(V156A)_gltA(M312I): CJL-8109 | 2.77 | 1.67 |
| CJL8109_pheA_R182A: CA13-8116 | 3.76 | 0.31 |

As shown in Table 9, it was confirmed that the L-leucine-producing strain *Corynebacterium glutamicum* CA13-8116 including the additional R182A variation in the pheA gene showed about 4-fold improvement in the L-leucine-producing ability, as compared to the parent strain *Corynebacterium glutamicum* ATCC13032. It was also confirmed that the L-leucine-producing strain *Corynebacterium glutamicum* CA13-8116 showed about 1.2-fold improvement in the L-leucine-producing ability, as compared to the parent strain *Corynebacterium glutamicum* CJL-8109. CA13-8116 showed about 5.4-fold reduction in the L-phenylalanine-producing ability, as compared to the parent strain *Corynebacterium glutamicum* CJL-8109.

These results indicate that the amino acid at position 182 of the amino acid sequence of pheA protein is an important site for increasing the L-leucine production.

Example 5: Examination of Leucine- and Phenylalanine-Producing Ability of Selected pheA Variation in Isoleucine-Producing Strain In order to examine whether the selected variation exhibits the effect on leucine and isoleucine, which is a representative branched-chain amino acid, an experiment was conducted to confirm the isoleucine producing ability by introducing the variation into an isoleucine-producing strain of the genus *Corynebacterium*. The detailed experimental method is as follows.

Example 5-1. Preparation of L-Isoleucine-Producing CA10-3101 Strain

An L-isoleucine-producing strain was developed from the wild-type *Corynebacterium glutamicum* ATCC13032. In detail, in order to release the feedback inhibition of threonine which is a precursor of isoleucine in the biosynthetic pathway, arginine which is an amino acid at position 407 of hom which is a gene encoding homoserine dehydrogenase, was substituted with histidine (US 2020-0340022 A1). In detail, to prepare strains into which the hom (R407H) variation was introduced, PCR was performed using the chromosome of *Corynebacterium glutamicum* ATCC13032 as a template and primers of SEQ ID NO: 17 and SEQ ID NO: 18 or SEQ ID NO: 19 and SEQ ID NO: 20. Sequences of the primers used here are shown in Table 10 below.

TABLE 10

| SEQ ID NO. | Sequence(5'->3') |
|---|---|
| SEQ ID NO: 17 | TCGAGCTCGGTACCCCGC TTTTGCACTCATCGAGC |
| SEQ ID NO: 18 | CACGATCAGATGTGCAT CATCAT |
| SEQ ID NO: 19 | ATGATGATGCACATCTG ATCGTG |
| SEQ ID NO: 20 | CTCTAGAGGATCCCCGAG CATCTTCCAAAACCTTG |

PfuUltra™ high-fidelity DNA polymerase (Stratagene) was used as the polymerase for the PCR reaction, and the PCR conditions included 28 cycles of denaturation at 95° C. for 30 seconds; annealing at 55° C. for 30 seconds; and polymerization at 72° C. for 1 minute. As a result, a DNA fragment of 1000 bp at the 5' upstream and a DNA fragment of 1000 bp at the 3' downstream, centering on the variation of the hom gene, were obtained, respectively. PCR was performed using the amplified two DNA fragments as templates and primers of SEQ ID NOS: 17 and 20. PCR was performed under conditions of denaturation at 95° C. for 5 minutes; 28 cycles of denaturation at 95° C. for 30 seconds, annealing at 55° C. for 30 seconds, and polymerization at 72° C. for 2 minutes; and polymerization at 72° C. for 5 minutes.

As a result, a DNA fragment of 2 kb was amplified, the DNA fragment including the hom gene variation encoding the homoserine dehydrogenase variant in which arginine at position 407 was substituted with histidine. The amplification product was purified using a PCR purification kit (QIAGEN) and used as an insert DNA fragment for the vector construction. The purified amplification product was treated with a restriction enzyme smal. pDCM2 vector heat-treated at 65° C. for 20 minutes and the amplification product, insert DNA fragment were made at a molar concentration (M) ratio of 1:2, and cloning was performed using an infusion cloning kit (TakaRa) according to the provided manual, thereby constructing a pDCM2-R407H vector for introducing the hom (R407H) variation into the chromosome.

The prepared vector was transformed into *Corynebacterium glutamicum* ATCC 13032 by electroporation, and subjected to secondary crossover, and a strain including the hom (R407H) variation on the chromosome was obtained and named *Corynebacterium glutamicum* ATCC13032 hom (R407H).

In order to release feedback inhibition by L-isoleucine and to increase activity in the prepared ATCC 13032 hom (R407H) strain, strains were prepared, into which variants (T381A, F383A) of ilvA which is a gene encoding L-threonine dehydratase were introduced. More specifically, to prepare strains into which ilvA (T381A, F383A) variations were introduced, PCR was performed using the chromosome of *Corynebacterium glutamicum* ATCC13032 as a template and primers of SEQ ID NO: 21 and SEQ ID NO: 22 or SEQ ID NO: 23 and SEQ ID NO: 24. Sequences of the primers used here are shown in Table 11 below.

TABLE 11

| SEQ ID NO. | Sequence(5'->3') |
|---|---|
| SEQ ID NO: 21 | TCGAGCTCGGTACCCATGAGTGAAACATACGTGTC |
| SEQ ID NO: 22 | GCGCTTGAGGTACTCtgcCAGCGcGATGTCATCATCCGG |
| SEQ ID NO: 23 | CCGGATGATGACATCgCGCTGgcaGAGTACCTCAAGCGC |
| SEQ ID NO: 24 | CTCTAGAGGATCCCCCGTCACCGACACCTCCACA |

PfuUltra™ high-fidelity DNA polymerase (Stratagene) was used as the polymerase for the PCR reaction, and the PCR conditions included 28 cycles of denaturation at 95° C. for 30 seconds; annealing at 55° C. for 30 seconds; and polymerization at 72° C. for 1 minute. As a result, a DNA fragment of 1126 bp at the 5' upstream and a DNA fragment of 286 bp at the 3' downstream, centering on the variation of the ilvA gene, were obtained, respectively. PCR was performed using the amplified two DNA fragments as templates and primers of SEQ ID NOS: 21 and 24. PCR was performed under conditions of denaturation at 95° C. for 5 minutes; 28 cycles of denaturation at 95° C. for 30 seconds, annealing at 55° C. for 30 seconds, and polymerization at 72° C. for 2 minutes; and polymerization at 72° C. for 5 minutes.

As a result, a DNA fragment of 1.4 kb was amplified, the DNA fragment including the ilvA gene variation encoding the threonine dehydratase variant in which threonine at position 381 was substituted with alanine, and phenylalanine at position 383 was substituted with alanine. The amplification product was purified using a PCR purification kit (QIAGEN) and used as an insert DNA fragment for the vector construction. The purified amplification product was treated with a restriction enzyme smaI. pDCM2 vector heat-treated at 65° C. for 20 minutes and the amplification product, insert DNA fragment were made at a molar concentration (M) ratio of 1:2, and cloning was performed using an infusion cloning kit (TakaRa) according to the provided manual, thereby constructing a pDCM2-ilvA (T381A, F383A) vector for introducing the ilvA (T381A, F383A) variations into the chromosome.

The prepared vector was transformed into *Corynebacterium glutamicum* ATCC13032 hom (R407H) by electroporation, and subjected to secondary crossover, and a strain including the ilvA (T381A, F383A) variations on the chromosome was obtained and named *Corynebacterium glutamicum* CA10-3101.

Example 5-2. Introduction of pheA Variant into CA10-3101 Strain and Evaluation The L-isoleucine-producing strain CA10-3101 was transformed with the pDCM2-pheA (R182A) vector prepared in Example 3-1, and the strains, in which each vector was inserted on the chromosome by recombination of the homologous sequence, were selected in a medium containing 25 mg/L kanamycin. The selected primary strains were again subjected to secondary crossover, and strains into which the target gene variation was introduced were selected. Finally, whether or not the pheA gene variation was introduced into the transformed strain was confirmed by performing PCR using primers of SEQ ID NO: 3 and SEQ ID NO: 4 of Table 1, and then analyzing the nucleotide sequence, thereby identifying that the pheA variation was introduced into the strain.

The L-isoleucine- and L-phenylalanine-producing ability of the prepared CA10-3101_pheA_R182A and ATCC13032, CA10-3101 strains was evaluated. The parent strain and the pheA variants were inoculated in a 250 ml corner-baffle flask containing 25 ml of an isoleucine production medium, respectively, and cultured at 32° C. for 60 hours under shaking at 200 rpm to produce L-isoleucine. The composition of the production medium used in this Example is as follows.

<Production Medium>

10% glucose, 0.2% yeast extract, 1.6% ammonium sulfate, 0.1% potassium phosphate monobasic, 0.1% magnesium sulfate heptahydrate, 10 mg/l iron sulfate heptahydrate, 10 mg/l manganese sulfate monohydrate, 200 μg/L biotin, pH 7.2

After completion of the culture, the production of L-isoleucine and L-phenylalanine was measured using high-performance liquid chromatography (HPLC), and the concentrations of L-isoleucine and by-products in the culture medium of each tested strain are shown in Table 12 below.

TABLE 12

| | L-isoleucine concentration (g/L) | L-Phe concentration (g/L) |
|---|---|---|
| ATCC13032 | 0.0 | 1.2 |
| CA10-3101 (parent strain) | 2.5 | 0.6 |
| CA10-3101_pheA_R182A | 3.0 | 0.2 |

As shown in Table 12, it was confirmed that the L-isoleucine-producing strain including the additional R182A variation in the pheA gene showed about 1.1-fold improvement in the L-isoleucine-producing ability, as compared to the parent strain *Corynebacterium glutamicum* CA10-3101, and CA10-3101_pheA_R182A strain showed a reduction in the by-product L-phenylalanine.

These results indicate that the amino acid at position 182 of the amino acid sequence of pheA protein is an important site for increasing the L-isoleucine production.

Example 6: Examination of Valine- and Phenylalanine-Producing Ability of Selected pheA Variation in Valine-Producing Strain In order to examine whether the selected variation also exhibits the effect on L-valine, which is a representative branched-chain amino acid, such as leucine, an experiment was conducted to confirm the valine- and phenylalanine-producing ability by introducing the selected variation into a valine-producing strain KCCM11201P of the genus *Corynebacterium*. The detailed experimental method is as follows.

Example 6-1. Introduction of pheA Variant into KCCM11201P Strain and Evaluation In order to examine whether or not the corresponding variation has an effect on increasing the L-valine-producing ability, an L-valine-producing strain *Corynebacterium glutamicum* KCCM11201P (U.S. Pat. No. 8,465,962 B2) was used. The valine-producing strain KCCM11201P was transformed with the pDCM2-pheA (R182A) vector prepared in Example 3-1, and the strains, in which each vector was inserted on the chromosome by recombination of the homologous sequence, were selected in a medium containing 25 mg/L kanamycin. The selected primary strains were again subjected to secondary crossover, and strains into which the target gene variation was introduced were selected. Finally, whether or not the pheA gene variation was introduced into the transformed strain was confirmed by performing PCR using primers of SEQ ID NO: 3 and SEQ ID NO: 4 of Table 1, and then analyzing the nucleotide sequence, thereby identifying that the pheA variation was introduced into the strain. The prepared strains were named KCCM11201P-pheA (R182A), respectively.

The valine-producing ability of the prepared KCCM11201P-pheA (R182A) strains was evaluated. In the same manner as in Example 2, flask culture was performed, and after completion of the culture, the valine production was measured by a method of using HPLC, and the culture results are as in Table 13 below.

TABLE 13

| Strain name | Val (g/L) | Phe (mg/L) |
|---|---|---|
| KCCM11201P | 2.60 | 146.62 |
| KCCM11201P - pheA(R182A) | 2.86 | 27.33 |

As shown in Table 13, it was confirmed that the L-valine-producing *Corynebacterium glutamicum* KCCM11201P-pheA (R182A) including the additional R182A variation in the pheA gene showed about 1.1-fold improvement in the L-valine-producing ability, as compared to the parent strain *Corynebacterium glutamicum* KCCM11201P. It was confirmed that KCCM11201P-pheA (R182A) showed about 5.36-fold reduction in the L-phenylalanine-producing ability, as compared to the parent strain *Corynebacterium glutamicum* KCCM11201P. These results indicate that the amino acid at position 182 of the amino acid sequence of pheA protein is an important site for increasing the L-valine production.

Reference Example 1: Examination of Effect of gitA (M312I) Variation on Leucine Production

Reference Example 1-1. Construction of Insertion Vector Including gitA Variation A vector for introducing gitA (M312I; SEQ ID NO: 25) variation was constructed using a site directed mutagenesis method.

PCR was performed using the chromosome of the wild-type *Corynebacterium glutamicum* as a template and a primer pair of SEQ ID NOS: 27 and 28 and a primer pair of SEQ ID NOS: 29 and 30.

PCR was performed under conditions of denaturation at 94° C. for 5 minutes, followed by 30 cycles of at 94° C. for 30 seconds, at 55° C. for 30 seconds, and at 72° C. for 1 minute 30 seconds, followed by polymerization at 72° C. for 5 minutes. The resultant gene fragment was cloned into a linear pDCM2 vector digested with Smal restriction enzyme using In-Fusion enzyme through fusion of the homologous sequence of the terminal 15 bases between DNA fragments, thereby constructing a pDCM2-gitA (M312I) vector substituting isoleucine for methionine which is an amino acid at position 312.

TABLE 14

| SEQ ID NO: | Primer | Sequence(5'->3') |
|---|---|---|
| 27 | gltA M3121 Up F | GTGAATTCGAGCTCGGTACCCG CGGGAATCCTGCGTTACCGC |
| 28 | gltA M3121 Up R | TGTAAACGCGGTGTCCGAAGCC GATGAGGCGGACGCCGTCTT |
| 29 | gltA M3121 Down F | AAGACGGCGTCCGCCTCATCGG CTTCGGACACCGCGTTTACA |
| 30 | gltA M3121 Down R | GGTCGACTCTAGAGGATCCCCT TAGCGCTCCTCGCGAGGAAC |

Reference Example 1-2. Introduction of Variant into ATCC13032 Strain and Evaluation The wild-type ATCC13032 was transformed with the pDCM2-gitA (M312I) vector prepared in Reference Example 1-1, and the strains, in which the vector was inserted on the chromosome by recombination of the homologous sequence, were selected in a medium containing 25 mg/L kanamycin. The selected primary strains were again subjected to secondary crossover, and strains into which the target gene variation was introduced were selected. Finally, whether or not the gitA gene variation was introduced into the transformed strain was confirmed by performing PCR using primers of SEQ ID NO: 15 and SEQ ID NO: 16 (Example 4-1, Table 8), and then analyzing the nucleotide sequence, thereby identifying that the variation (SEQ ID NO: 26) was introduced into the strain. The prepared strain was named ATCC13032_gltA_M312I.

To evaluate the leucine-producing ability of the prepared ATCC13032_gltA_M312I strain, a flask fermentation titer was evaluated. Each one platinum loop of the parent strain *Corynebacterium glutamicum* ATCC13032 and the prepared ATCC13032_gltA_M312I was inoculated into a 250 ml corner-baffle flask containing 25 ml of a production medium, and then cultured at 30° C. for 60 hours under shaking at 200 rpm to produce leucine. After completion of the culture, the leucine production was measured by HPLC. The concentration of leucine in the culture medium of each tested strain is shown in Table 15 below.

Production medium: 100 g of glucose, 40 g of $(NH_4)_2$ $SO_4$, 2.5 g of soy protein, 5 g of corn steep solids, 3 g of urea, 1 g of $KH_2PO_4$, 0.5 g of $MgSO_4·7H_2O$, 100 μg of biotin, 1,000 μg of thiamine hydrochloride, 2000

µg of calcium-pantothenic acid, 3,000 µg of nicotinamide, 30 g of CaCO$_3$ (Based on 1 liter of distilled water), pH 7.0

TABLE 15

| Strain name | Leucine (g/L) |
| --- | --- |
| ATCC13032 | 0.87 |
| ATCC13032_gltA_M312I | 1.25 |

From this, it was confirmed that the M312I substitution of gitA is an effective variation for increasing the leucine production.

Reference Example 2: Examination of Effect of ilvA (T381A, F383A) Variations on Isoleucine Production

Reference Example 2-1. Construction of pECCG117-ilvA (F383A)

To amplify ilvA (SEQ ID NO: 32) which is a gene encoding threonine dehydratase (SEQ ID NO: 31), BamHI restriction enzyme sites were inserted at both ends of primers (SEQ ID NO: 33 and SEQ ID NO: 34) for amplification from the promoter region (about 300 bp upstream the start codon) to the terminator region (about 100 bp downstream the stop codon), based on the previously reported ilvA sequence introduced with the F383A variation (World J Microbiol Biotechnol (2015) 31:1369-1377). In addition, primers (SEQ ID NO: 35 and SEQ ID NO: 36) for introducing the F383A variation into ilvA were used. Sequences of primers used here are shown in Table 16 below.

TABLE 16

| SEQ ID NO: | Name | Sequence |
| --- | --- | --- |
| 33 | Primer 1 | ggatccGACTGAG CCTGGGCAACTGG |
| 34 | Primer 2 | ggatccCCGTCAC CGACACCTCCACA |
| 35 | Primer 3 | ACATCACGCTGgc aGAGTACCTCAA |
| 36 | Primer 4 | TTGAGGTACTCtg cCAGCGTGATGT |

PCR was performed using the chromosome of the wild-type *Corynebacterium glutamicum* ATCC 13032 as a template and primers of SEQ ID NO: 33 and SEQ ID NO: 34. SEQ ID NO: 35 and SEQ ID NO: 36. PCR was performed under conditions of denaturation at 95° C. for 5 minutes, followed by 30 cycles of denaturation at 95° C. for 30 seconds, annealing at 55° C. for 30 seconds, and polymerization at 72° C. for 90 seconds, and then polymerization at 72° C. for 5 minutes.

As a result, a DNA fragment of 1460 bp at the 5' upstream and a DNA fragment of 276 bp at the 3' downstream, centering on the variation of the ilvA gene, were obtained, respectively.

PCR was performed using the amplified two DNA fragments as templates and primers of SEQ ID NO: 35 and SEQ ID NO: 36.

As a result, a DNA fragment of 1531 bp, including the ilvA variation substituting alanine for phenylalanine at position 383, was amplified. pECCG117 (Korean Patent No. 10-0057684) vector and the ilvA DNA fragment were treated with a restriction enzyme BamHI, and ligated using DNA ligase, and then cloned to obtain a plasmid, which was named pECCG117-ilvA (F383A).

Reference Example 2-2: Additional Introduction of Random Mutation into pECCG117-ilvA (F383A)

To obtain a variant of the gene encoding L-threonine dehydratase, an ilvA variant gene plasmid was prepared using a random mutagenesis kit (Agilent Technologies, USA). PCR was performed using the ilvA (F383A) chromosome of Reference Example 2-1 as a template and primers of SEQ ID NO: 35 and SEQ ID NO: 36. PCR was performed under conditions of denaturation at 95° C. for 2 minutes, followed by 30 cycles of denaturation at 95° C. for 30 seconds, annealing at 55° C. for 30 seconds, and polymerization at 72° C. for 90 seconds, and then polymerization at 72° C. for 10 minutes.

As a result, a DNA fragment of 1531 bp was amplified, which is an ilvA variant encoding L-threonine dehydratase with an additional random variation, in addition to the variation in which phenylalanine at position 383 was substituted with alanine. The pECCG117 vector and the ilvA variant DNA fragment were treated with a restriction enzyme BamHI, ligated using DNA ligase, and then cloned to obtain a plasmid group.

Reference Example 2-3: Preparation of CJILE-301 Strain pECCG117-ilvA (F383A) was introduced into the wild-type *Corynebacterium glutamicum* ATCC13032 hom (R407H) strain, and the strain into which the prepared plasmid was introduced was named ATCC13032 hom (R407H)/pECCG117-ilvA (F383A). In addition, the variant plasmid group obtained in Reference Example 2-2 was introduced into *Corynebacterium glutamicum* ATCC13032 hom (R407H) strain, which was then spread on a minimal medium. A death rate was obtained, and as a result, the death rate was 70%, and the living cells were inoculated and cultured in a seed medium, and finally, a variant strain showing the higher isoleucine-producing ability than the control ATCC13032 hom (R407H)/pECCG117-ilvA (F383A) was selected, and named *Corynebacterium glutamicum* CJILE-301.

The plasmid was isolated from the CJILE-301 strain, and the ilvA gene was sequenced. As a result, it was confirmed that A which is a base sequence at position 1141 of the ilvA gene was substituted with G, encoding a variant protein having a substitution of A for T at position 381 of ilvA protein, in addition to the substitution of A for F at position 383 of ilvA protein. The sequence was represented by SEQ ID NO: 38.

Reference Example 2-4: Introduction of ilvA Variant (T381A, F383A)

To introduce the ilvA variant (T381A, F383A) into the wild-type strain, primers of SEQ ID NO: 21 and SEQ ID NO: 24 (Example 5-1, Table 11) were prepared.

To prepare a strain into which the IlvA variant (T381A, F383A) was introduced, PCR was performed using a plasmid DNA extracted from the CJILE-301 strain as a template and primers of SEQ ID NO: 21 and SEQ ID NO: 24.

PfuUltra™ high-fidelity DNA polymerase (Stratagene) was used as the polymerase for the PCR reaction, and the PCR conditions included 28 cycles of denaturation at 95° C. for 30 seconds; annealing at 55° C. for 30 seconds; and polymerization at 72° C. for 2 minutes.

As a result, a gene fragment of 1411 bp, including the terminator region of about 100 bp of the ilvA gene of 1311 bp, was obtained.

The amplification product was purified using a PCR purification kit, and used as an insert DNA fragment for the vector construction. The purified amplification product was treated with a restriction enzyme smal. pDCM2 vector heat-treated at 65° C. for 20 minutes and the amplification product, insert DNA fragment were made at a molar concentration (M) ratio of 1:2, and cloning was performed using an infusion cloning kit according to the provided manual, thereby constructing a pDCM2-T381A_F383A vector for introducing the T381A, F383A variations into the chromosome.

The prepared vector was transformed into *Corynebacterium glutamicum* ATCC13032 hom (R407H) by electroporation, and subjected to secondary crossover, and a strain including the ilvA (T381A, F383A; SEQ ID NO: 37) variations on the chromosome was obtained and named CA10-3101.

The strain CA10-3101 was deposited at the Korean Culture Center of Microorganisms (KCCM), an international depository authority under the Budapest Treaty, on May 27, 2020, and assigned Accession No. KCCM12739P.

The KCCM12739P strain was inoculated in a 250 ml corner-baffle flask containing 25 ml of an isoleucine production medium, and then cultured at 32° C. for 60 hours under shaking at 200 rpm to produce L-isoleucine. The composition of the used production medium is as follows.

<Production Medium>

10% glucose, 0.2% yeast extract, 1.6% ammonium sulfate, 0.1% potassium phosphate monobasic, 0.1% magnesium sulfate heptahydrate, 10 mg/L iron sulfate heptahydrate, 10 mg/L manganese sulfate monohydrate, 200 g/L biotin, pH 7.2

After completion of the culture, the concentrations of L-isoleucine and L-threonine in the culture medium were measured using high-performance liquid chromatography (HPLC), and the results are shown in Table 17 below.

TABLE 17

| Strain name | L-isoleucine (g/L) | L-threonine (g/L) |
|---|---|---|
| ATCC13032 hom(R407H) | 0.0 | 3.8 |
| ATCC13032 hom(R407H) ilvA(WT) | 0.0 | 3.7 |
| CA10-3101(ATCC13032 hom(R407H) ilvA(T381A, F383A)) | 3.3 | 0.0 |

As shown in Table 17, it was confirmed that the parent strain *Corynebacterium glutamicum* ATCC 13032 hom (R407H) could not produce L-isoleucine, whereas the ATCC13032 hom (R407H) ilvA (T381A, F383A) variant strain produced L-isoleucine at a concentration of 3.9 g/L to exhibit a remarkable increase in the L-isoleucine productivity, as compared to the parent strain.

From this, it was confirmed that the ilvA (T381A, F383A) variation is an effective variation for increasing the isoleucine production.

Reference Example 3: Examination of Effect of leuA (P247C, R558H, G561D) on Leucine Production Reference Example 3-1. Preparation of CJL-8100 Strain pDCM2-leuA (R558H, G561D) vector including leuA gene variations, as disclosed in KR 10-2018-0077008A, was transformed into the wild-type *Corynebacterium glutamicum* ATCC13032 by electroporation, and the strains, in which the vector was inserted on the chromosome by recombination of the homologous sequence, were selected in a medium containing 25 mg/L kanamycin. The selected primary strains were again subjected to secondary crossover, and strains into which the leuA gene variation was introduced were selected. Finally, whether or not the variation was introduced into the transformed strain was confirmed by performing PCR (at 94° C. for 5 minutes, followed by 30 cycles of at 94° C. for 30 seconds/at 55° C. for 30 seconds/at 72° C. for 90 seconds, at 72° C. for 5 minutes) using primers of SEQ ID NO: 39 and SEQ ID NO: 43, and then analyzing the nucleotide sequence, thereby identifying that the R558H, G561D variations were introduced. ATCC13032_leuA_ (R558H, G561D) strain transformed with the pDCM2-leuA (R558H, G561D) vector was named 'CJL-8100'.

Sequences of the primers used in Reference Example 3 are shown in Table 18 below.

TABLE 18

| SEQ ID NO. | Sequence(5'->3') |
|---|---|
| SEQ ID NO: 39 | AACACGACCGGCATCCCGTCGC |
| SEQ ID NO: 40 | AAATCATTTGAGAAAACTCGAGG |
| SEQ ID NO: 41 | GTGAATTCGAGCTCGGTACCCAA ATCATTTGAGAAAACTCGAGGC |
| SEQ ID NO: 42 | GGTGATCATCTCAACGGTGGAAC ACAGGTTGATGATCATTGGGTT |
| SEQ ID NO: 43 | AACCCAATGATCATCAACCTGTG TTCCACCGTTGAGATGATCACC |
| SEQ ID NO: 44 | GGTCGACTCTAGAGGATCCCCA AGAAGGCAACATCGGACAGC |
| SEQ ID NO: 45 | ATCCATTCAATGGAGTCTGCG |

Reference Example 3-2. Construction of Insertion Vector Including leuA Variation A vector for introducing P247C variation into an L-leucine-producing strain CJL-8100, in which two variations (R558H, G561D) were introduced into LeuA, was constructed.

PCR was performed using the chromosome of CJL-8100 strain as a template and a primer pair of SEQ ID NOS: 39 and 40 and a primer pair of SEQ ID NOS: 41 and 42. PCR was performed under conditions of denaturation at 94° C. for 5 minutes, followed by 30 cycles of at 94° C. for 30 seconds, at 55° C. for 30 seconds, and at 72° C. for 1 minute and 30 seconds, and then at 72° C. for 5 minutes. The resultant PCR fragment was cloned into a linear pDCM2 vector digested with Smal restriction enzyme using In-Fusion enzyme through fusion of the homologous sequence of the terminal 15 bases between DNA fragments, thereby constructing a pDCM2-leuA (P247C, R558H, G561D) vector including the leuA variation encoding the LeuA variant in which histidine was substituted for arginine which is an amino acid at position 558 of the LeuA amino acid sequence of the wild-type strain, and aspartic acid was substituted for glycine which is an amino acid at position 561, and substituting cysteine (Cys) for proline (Pro) which is an amino acid at position 247 of LeuA.

Reference Example 3-3. Introduction of LeuA Variant (P247C) into CJL-8100 Strain and Evaluation CJL-8100 which is an L-leucine-producing strain was transformed with the pDCM2-leuA (P247C, R558H, G561D) vector prepared in Reference Example 3-2, and the strains, in which the vector was inserted on the chromosome by recombination of the homologous sequence, were selected in a medium containing 25 mg/L kanamycin. The selected primary strains were again subjected to secondary crossover, and strains into which the target gene variation was introduced were selected. Finally, whether or not the leuA gene variation was introduced into the transformed strain was confirmed by performing PCR (at 94° C. for 5 minutes, followed by 30 cycles of at 94° C. for 30 seconds/at 55° C. for 30 seconds/at 72° C. for 90 seconds, and then at 72° C. for 5 minutes) using primers of SEQ ID NO: 39 and SEQ ID NO: 45, and then analyzing the nucleotide sequence. As a result of sequencing analysis, it was confirmed that leuA variations were introduced into the strain, the leuA variations encoding the LeuA variant (P247C, R558H, G561D), in which histidine was substituted for arginine which is an amino acid at position 558 of LeuA, aspartic acid was substituted for glycine which is an amino acid at position 561 of LeuA, and cysteine (Cys) was substituted for proline (Pro) which is an amino acid at position 247 of LeuA by substitution of A for G which is a nucleotide at position 1673, substitution of AT for GC which are nucleotides at positions 1682 and 1683, and substitution of TG for CC which are nucleotides at positions 739 and 740 of the leuA gene in the chromosome of the strain. The prepared CJL8100_leuA_P247C was named 'CA13-8105', and deposited at the Korean Culture Center of Microorganisms (KCCM), an international depository authority under the Budapest Treaty, on Apr. 29, 2020, and assigned Accession No. KCCM12709P.

The amino acid sequence of the LeuA variant (P247C, R558H, G561D) including a total of 3 types of variations, and base sequence of the leuA variant encoding the same are as in SEQ ID NO: 46 and SEQ ID NO: 47, respectively.

The L-leucine-producing ability of ATCC13032, the prepared CJL-8100 and CA13-8105 strains was evaluated. In detail, a flask culture was performed in the same manner as in Example 2-1. After completion of the culture, the L-leucine productions of the parent strain and variant strains were measured by HPLC, and the results are shown in Table 19 below.

TABLE 19

| Strain name | L-leucine (g/L) |
| --- | --- |
| ATCC13032 | 0.87 |
| ATCC13032_leuA_(R558H, G561D): CJL-8100 | 2.71 |
| CJL8100_leuA_P247C: CA13-8105 | 3.52 |

As shown in Table 19, the L-leucine-producing strain *Corynebacterium glutamicum* CJL8100 showed about 130% improvement in the L-leucine-producing ability, as compared to the parent strain ATCC13032. The CA13-8105 strain prepared by introducing the additional leuA_P247C variation into the CJL8100 strain showed about 150% improvement in the L-leucine-producing ability, as compared to the parent strain CJL8100.

From this, it was confirmed that the leuA (R558H, G561D, P247C) variations are effective variations for increasing the leucine production.

Based on the above description, it will be understood by those skilled in the art that the present disclosure may be implemented in a different specific form without changing the technical spirit or essential characteristics thereof. In this regard, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds are therefore intended to be embraced by the claims.

Effect of the Invention

When a prephenate dehydratase variant of the present disclosure is used, it is possible to produce branched-chain amino acids in a high yield, as compared to no use thereof.

What is claimed is:

1. A prephenate dehydratase variant, wherein an amino acid corresponding to position 182 from the N-terminus of the amino acid sequence of SEQ ID NO: 1 is substituted with an amino acid other than arginine, and wherein the prephenate dehydratase variant has 90% or more sequence identity to the amino acid sequence of SEQ ID NO: 1.

2. The prephenate dehydratase variant of claim 1, wherein the substitution with another amino acid is a substitution with a non-polar amino acid or a small-size amino acid.

3. The prephenate dehydratase variant of claim 1, wherein another amino acid is alanine (Ala).

4. The prephenate dehydratase variant of claim 1, wherein the prephenate dehydratase variant has 99% or more sequence identity to SEQ ID NO: 5.

5. The prephenate dehydratase variant of claim 1, wherein the prephenate dehydratase variant has a weakened activity, as compared to the prephenate dehydratase of SEQ ID NO: 1.

6. A polynucleotide encoding the prephenate dehydratase variant of claim 1.

7. A vector comprising the polynucleotide of claim 6.

8. A microorganism of the genus *Corynebacterium*, the microorganism comprising one or more of the prephenate dehydratase variant of claim 1; a polynucleotide encoding the prephenate dehydratase variant; and a vector including the polynucleotide.

9. The microorganism of claim 8, wherein the microorganism is *Corynebacterium glutamicum*.

10. The microorganism of claim 8, wherein the microorganism is for producing branched-chain amino acids.

11. The microorganism of claim 10, wherein the branched-chain amino acids are one or more selected from L-leucine, L-isoleucine, and L-valine.

12. A method of producing branched-chain amino acids, the method comprising a step of culturing the microorganism of claim 7 in a medium.

13. The method of claim 12, further comprising a step of recovering the branched-chain amino acids from the microorganism or from the medium.

14. The method of claim 13, wherein the branched-chain amino acids are one or more selected from L-leucine, L-isoleucine, and L-valine.

* * * * *

SEQUENCE LISTING

```
<160> NUMBER OF SEQ ID NOS: 47

<210> SEQ ID NO 1
<211> LENGTH: 315
<212> TYPE: PRT
<213> ORGANISM: Artificial Sequence
<220> FEATURE:
<223> OTHER INFORMATION: PheA_WT

<400> SEQUENCE: 1

Met Ser Asp Ala Pro Thr Val Val Ala Tyr Leu Gly Pro Ala Gly Thr
1               5                   10                  15

Phe Thr Glu Glu Ala Leu Tyr Lys Phe Ala Asp Ala Gly Val Phe Gly
            20                  25                  30

Asp Gly Glu Ile Glu Gln Leu Pro Ala Lys Ser Pro Gln Glu Ala Val
        35                  40                  45
```

```
Asp Ala Val Arg His Gly Thr Ala Gln Phe Ala Val Val Ala Ile Glu
    50              55                  60

Asn Phe Val Asp Gly Pro Val Thr Pro Thr Phe Asp Ala Leu Asp Gln
65              70                  75                  80

Gly Ser Asn Val Gln Ile Ile Ala Glu Glu Glu Leu Asp Ile Ala Phe
                85                  90                  95

Ser Ile Met Val Arg Pro Gly Thr Ser Leu Ala Asp Val Lys Thr Leu
            100                 105                 110

Ala Thr His Pro Val Gly Tyr Gln Gln Val Lys Asn Trp Met Ala Thr
            115                 120                 125

Thr Ile Pro Asp Ala Met Tyr Leu Ser Ala Ser Ser Asn Gly Ala Gly
    130                 135                 140

Ala Gln Met Val Ala Glu Gly Thr Ala Asp Ala Ala Ala Pro Ser
145                 150                 155                 160

Arg Ala Ala Glu Leu Phe Gly Leu Glu Arg Leu Val Asp Asp Val Ala
                165                 170                 175

Asp Val Arg Gly Ala Arg Thr Arg Phe Val Ala Val Gln Ala Gln Ala
            180                 185                 190

Ala Val Ser Glu Pro Thr Gly His Asp Arg Thr Ser Val Ile Phe Ser
            195                 200                 205

Leu Pro Asn Val Pro Gly Ser Leu Val Arg Ala Leu Asn Glu Phe Ala
    210                 215                 220

Ile Arg Gly Val Asp Leu Thr Arg Ile Glu Ser Arg Pro Thr Arg Lys
225                 230                 235                 240

Val Phe Gly Thr Tyr Arg Phe His Leu Asp Ile Ser Gly His Ile Arg
                245                 250                 255

Asp Ile Pro Val Ala Glu Ala Leu Arg Ala Leu His Leu Gln Ala Glu
            260                 265                 270

Glu Leu Val Phe Val Gly Ser Trp Pro Ser Asn Arg Ala Glu Asp Ser
            275                 280                 285

Thr Pro Gln Thr Asp Gln Leu Ala Lys Leu His Lys Ala Asp Glu Trp
    290                 295                 300

Val Arg Ala Ala Ser Glu Gly Arg Lys Leu Asn
305                 310                 315
```

<210> SEQ ID NO 2
<211> LENGTH: 948
<212> TYPE: DNA
<213> ORGANISM: Artificial Sequence
<220> FEATURE:
<223> OTHER INFORMATION: pheA_WT

<400> SEQUENCE: 2

```
atgagcgacg caccaactgt tgtggcctat ttggggcctg ccggaacctt caccgaagaa      60
gccctctaca aatttgccga cgccggcgta ttcggcgacg tgagatcga gcagctacca     120 gccaaatcgc cacaagaagc tgtcgacgcc gtccgccacg gcaccgccca gttcgcggtg     180
gtcgccatcg aaaacttcgt cgacggcccc gtcaccccca ccttcgacgc ccttgaccag     240
ggctccaacg tgcaaatcat cgccgaagaa gaactcgaca tcgccttttc catcatggtc     300
cggccaggga cttcgcttgc cgacgtcaaa accctcgcca cccacccggt tgggtaccaa     360
caagtgaaaa actggatggc aaccaccatt ccggacgcca tgtatctttc agcaagctcc     420
aacggcgccg gcgcacaaat ggttgccgaa ggaaccgccg acgcagccgc agcgccctcc     480
cgcgcagccg aactcttcgg actggaacgc cttgttgatg atgtcgccga cgtccgtggc     540
```

-continued

```
gcccgcaccc gcttcgttgc tgtccaagcc caagcagccg tttccgaacc gaccggccac      600
gaccgcacct ccgtcatttt ctccctaccg aatgtgccag gcagcctcgt gcgcgccctc      660
aacgaattcg ccatccgcgg cgttgacctc acccgcatcg aatcccgccc cacccgcaaa      720
gtcttcggaa cctaccgctt ccacctggac atatccggac atatccgcga tatccccgtc      780
gccgaagccc tccgcgcact ccacctccaa gccgaagaac tcgtcttcgt cggctcctgg      840
ccctccaacc gtgcggaaga cagcacgccc caaaccgacc aactagctaa gctacacaag      900
gcggacgaat gggttcgcgc agcaagcgaa ggaaggaaac ttaactag                   948
```

<210> SEQ ID NO 3
<211> LENGTH: 17
<212> TYPE: DNA
<213> ORGANISM: Artificial Sequence
<220> FEATURE:
<223> OTHER INFORMATION: primer

<400> SEQUENCE: 3

```
ttgaggtcct tggctgg                                                      17
```

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4

```
cgcaacacga tggagctg                                                     18
```

<210> SEQ ID NO 5
<211> LENGTH: 315
<212> TYPE: PRT
<213> ORGANISM: Artificial Sequence
<220> FEATURE:
<223> OTHER INFORMATION: PheA_R182A

<400> SEQUENCE: 5

```
Met Ser Asp Ala Pro Thr Val Val Ala Tyr Leu Gly Pro Ala Gly Thr
1               5                   10                  15

Phe Thr Glu Glu Ala Leu Tyr Lys Phe Ala Asp Ala Gly Val Phe Gly
            20                  25                  30

Asp Gly Glu Ile Glu Gln Leu Pro Ala Lys Ser Pro Gln Glu Ala Val
        35                  40                  45

Asp Ala Val Arg His Gly Thr Ala Gln Phe Ala Val Val Ala Ile Glu
    50                  55                  60

Asn Phe Val Asp Gly Pro Val Thr Pro Thr Phe Asp Ala Leu Asp Gln
65                  70                  75                  80

Gly Ser Asn Val Gln Ile Ile Ala Glu Glu Glu Leu Asp Ile Ala Phe
                85                  90                  95

Ser Ile Met Val Arg Pro Gly Thr Ser Leu Ala Asp Val Lys Thr Leu
            100                 105                 110

Ala Thr His Pro Val Gly Tyr Gln Gln Val Lys Asn Trp Met Ala Thr
        115                 120                 125

Thr Ile Pro Asp Ala Met Tyr Leu Ser Ala Ser Asn Gly Ala Gly
        130                 135                 140

Ala Gln Met Val Ala Glu Gly Thr Ala Asp Ala Ala Ala Pro Ser
145                 150                 155                 160
```

```
Arg Ala Ala Glu Leu Phe Gly Leu Glu Arg Leu Val Asp Asp Val Ala
            165                 170                 175

Asp Val Arg Gly Ala Ala Thr Arg Phe Val Ala Val Gln Ala Gln Ala
            180                 185                 190

Ala Val Ser Glu Pro Thr Gly His Asp Arg Thr Ser Val Ile Phe Ser
            195                 200                 205

Leu Pro Asn Val Pro Gly Ser Leu Val Arg Ala Leu Asn Glu Phe Ala
        210                 215                 220

Ile Arg Gly Val Asp Leu Thr Arg Ile Glu Ser Arg Pro Thr Arg Lys
225                 230                 235                 240

Val Phe Gly Thr Tyr Arg Phe His Leu Asp Ile Ser Gly His Ile Arg
                245                 250                 255

Asp Ile Pro Val Ala Glu Ala Leu Arg Ala Leu His Leu Gln Ala Glu
            260                 265                 270

Glu Leu Val Phe Val Gly Ser Trp Pro Ser Asn Arg Ala Glu Asp Ser
            275                 280                 285

Thr Pro Gln Thr Asp Gln Leu Ala Lys Leu His Lys Ala Asp Glu Trp
        290                 295                 300

Val Arg Ala Ala Ser Glu Gly Arg Lys Leu Asn
305                 310                 315
```

```
<210> SEQ ID NO 6
<211> LENGTH: 948
<212> TYPE: DNA
<213> ORGANISM: Artificial Sequence
<220> FEATURE:
<223> OTHER INFORMATION: pheA_R182A

<400> SEQUENCE: 6
atgagcgacg caccaactgt tgtggcctat ttggggcctg ccggaacctt caccgaagaa      60
gccctctaca aatttgccga cgccggcgta ttcggcgacg gtgagatcga gcagctacca     120
gccaaatcgc cacaagaagc tgtcgacgcc gtccgccacg gcaccgccca gttcgcggtg     180
gtcgccatcg aaaacttcgt cgacggcccc gtcacccca ccttcgacgc ccttgaccag     240
ggctccaacg tgcaaatcat cgccgaagaa gaactcgaca tcgcctttc catcatggtc     300 cggccaggga cttcgcttgc cgacgtcaaa accctcgcca cccacccggt tgggtaccaa     360
caagtgaaaa actggatggc aaccaccatt ccggacgcca tgtatctttc agcaagctcc     420
aacggcgccg gcgcacaaat ggttgccgaa ggaaccgccg acgcagccgc agcgccctcc     480
cgcgcagccg aactcttcgg actggaacgc cttgttgatg atgtcgccga cgtccgtggc     540
gccgcgaccc gcttcgttgc tgtccaagcc caagcagccg tttccgaacc gaccggccac     600
gaccgcacct ccgtcatttt ctccctaccg aatgtgccag gcagcctcgt gcgcgccctc     660
aacgaattcg ccatccgcgg cgttgacctc acccgcatcg aatcccgccc cacccgcaaa     720
gtcttcggaa cctaccgctt ccacctggac atatccggac atatccgcga tatccccgtc     780
gccgaagccc tccgcgcact ccacctccaa gccgaagaac tcgtcttcgt cggctcctgg     840
ccctccaacc gtgcggaaga cagcacgccc caaaccgacc aactagctaa gctacacaag     900
gcggacgaat gggttcgcgc agcaagcgaa ggaaggaaac ttaactag                  948
```

```
<210> SEQ ID NO 7
<211> LENGTH: 38
<212> TYPE: DNA
<213> ORGANISM: Artificial Sequence
<220> FEATURE:
<223> OTHER INFORMATION: primer
```

<400> SEQUENCE: 7
gtgaattcga gctcggtacc cgtggcatgg atgaaaag                                38

<210> SEQ ID NO 8
<211> LENGTH: 36
<212> TYPE: DNA
<213> ORGANISM: Artificial Sequence
<220> FEATURE:
<223> OTHER INFORMATION: primer

<400> SEQUENCE: 8
ttggacagca acgaagcggg tcgcggcgcc acggac                                  36

<210> SEQ ID NO 9
<211> LENGTH: 37
<212> TYPE: DNA
<213> ORGANISM: Artificial Sequence
<220> FEATURE:
<223> OTHER INFORMATION: primer

<400> SEQUENCE: 9
gtcgccgacg tccgtggcgc cgcgacccgc ttcgttg                                 37

<210> SEQ ID NO 10
<211> LENGTH: 38
<212> TYPE: DNA
<213> ORGANISM: Artificial Sequence
<220> FEATURE:
<223> OTHER INFORMATION: primer

<400> SEQUENCE: 10
ggtcgactct agaggatccc cgtggctgtc catgattc                                38

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
tatgcttcac cacatgactt c                                                  21

<210> SEQ ID NO 12
<211> LENGTH: 23
<212> TYPE: DNA
<213> ORGANISM: Artificial Sequence
<220> FEATURE:
<223> OTHER INFORMATION: primer

<400> SEQUENCE: 12
aaatcatttg agaaaactcg agg                                                23

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
gtcacccgat cgtctgaag                                                     19

<210> SEQ ID NO 14

```
<211> LENGTH: 18
<212> TYPE: DNA
<213> ORGANISM: Artificial Sequence
<220> FEATURE:
<223> OTHER INFORMATION: primer

<400> SEQUENCE: 14
gtcttaaaac cggttgat                                                      18

<210> SEQ ID NO 15
<211> LENGTH: 19
<212> TYPE: DNA
<213> ORGANISM: Artificial Sequence
<220> FEATURE:
<223> OTHER INFORMATION: primer

<400> SEQUENCE: 15
caatgctggc tgcgtacgc                                                     19

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
ctcctcgcga ggaaccaact                                                    20

<210> SEQ ID NO 17
<211> LENGTH: 35
<212> TYPE: DNA
<213> ORGANISM: Artificial Sequence
<220> FEATURE:
<223> OTHER INFORMATION: primer

<400> SEQUENCE: 17
tcgagctcgg taccccgctt ttgcactcat cgagc                                   35

<210> SEQ ID NO 18
<211> LENGTH: 23
<212> TYPE: DNA
<213> ORGANISM: Artificial Sequence
<220> FEATURE:
<223> OTHER INFORMATION: primer

<400> SEQUENCE: 18
cacgatcaga tgtgcatcat cat                                                 23

<210> SEQ ID NO 19
<211> LENGTH: 23
<212> TYPE: DNA
<213> ORGANISM: Artificial Sequence
<220> FEATURE:
<223> OTHER INFORMATION: primer

<400> SEQUENCE: 19
atgatgatgc acatctgatc gtg                                                 23

<210> SEQ ID NO 20
<211> LENGTH: 35
<212> TYPE: DNA
<213> ORGANISM: Artificial Sequence
<220> FEATURE:
<223> OTHER INFORMATION: primer

<400> SEQUENCE: 20
```
ctctagagga tccccgagca tcttccaaaa ccttg                              35

```
<210> SEQ ID NO 21
<211> LENGTH: 35
<212> TYPE: DNA
<213> ORGANISM: Artificial Sequence
<220> FEATURE:
<223> OTHER INFORMATION: primer

<400> SEQUENCE: 21
```
tcgagctcgg tacccatgag tgaaacatac gtgtc                              35

```
<210> SEQ ID NO 22
<211> LENGTH: 39
<212> TYPE: DNA
<213> ORGANISM: Artificial Sequence
<220> FEATURE:
<223> OTHER INFORMATION: primer

<400> SEQUENCE: 22
```
gcgcttgagg tactctgcca gcgcgatgtc atcatccgg                          39

```
<210> SEQ ID NO 23
<211> LENGTH: 39
<212> TYPE: DNA
<213> ORGANISM: Artificial Sequence
<220> FEATURE:
<223> OTHER INFORMATION: primer

<400> SEQUENCE: 23
```
ccggatgatg acatcgcgct ggcagagtac ctcaagcgc                          39

```
<210> SEQ ID NO 24
<211> LENGTH: 34
<212> TYPE: DNA
<213> ORGANISM: Artificial Sequence
<220> FEATURE:
<223> OTHER INFORMATION: primer

<400> SEQUENCE: 24
```
ctctagagga tccccccgtca ccgacacctc caca                             34

```
<210> SEQ ID NO 25
<211> LENGTH: 437
<212> TYPE: PRT
<213> ORGANISM: Artificial Sequence
<220> FEATURE:
<223> OTHER INFORMATION: GltA_M312I

<400> SEQUENCE: 25
```

Met Phe Glu Arg Asp Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
    50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

```
Leu Leu Ile Asn Gly Glu Leu Pro Thr Pro Asp Glu Leu His Lys Phe
            100             105             110

Asn Asp Glu Ile Arg His His Thr Leu Leu Asp Glu Asp Phe Lys Ser
            115             120             125

Gln Phe Asn Val Phe Pro Arg Asp Ala His Pro Met Ala Thr Leu Ala
            130             135             140

Ser Ser Val Asn Ile Leu Ser Thr Tyr Tyr Gln Asp Gln Leu Asn Pro
145             150             155             160

Leu Asp Glu Ala Gln Leu Asp Lys Ala Thr Val Arg Leu Met Ala Lys
            165             170             175

Val Pro Met Leu Ala Ala Tyr Ala His Arg Ala Arg Lys Gly Ala Pro
            180             185             190

Tyr Met Tyr Pro Asp Asn Ser Leu Asn Ala Arg Glu Asn Phe Leu Arg
            195             200             205

Met Met Phe Gly Tyr Pro Thr Glu Pro Tyr Glu Ile Asp Pro Ile Met
            210             215             220

Val Lys Ala Leu Asp Lys Leu Leu Ile Leu His Ala Asp His Glu Gln
225             230             235             240

Asn Cys Ser Thr Ser Thr Val Arg Met Ile Gly Ser Ala Gln Ala Asn
            245             250             255

Met Phe Val Ser Ile Ala Gly Gly Ile Asn Ala Leu Ser Gly Pro Leu
            260             265             270

His Gly Gly Ala Asn Gln Ala Val Leu Glu Met Leu Glu Asp Ile Lys
            275             280             285

Ser Asn His Gly Gly Asp Ala Thr Glu Phe Met Asn Lys Val Lys Asn
            290             295             300

Lys Glu Asp Gly Val Arg Leu Ile Gly Phe Gly His Arg Val Tyr Lys
305             310             315             320

Asn Tyr Asp Pro Arg Ala Ala Ile Val Lys Glu Thr Ala His Glu Ile
            325             330             335

Leu Glu His Leu Gly Gly Asp Asp Leu Leu Asp Leu Ala Ile Lys Leu
            340             345             350

Glu Glu Ile Ala Leu Ala Asp Asp Tyr Phe Ile Ser Arg Lys Leu Tyr
            355             360             365

Pro Asn Val Asp Phe Tyr Thr Gly Leu Ile Tyr Arg Ala Met Gly Phe
    370             375             380

Pro Thr Asp Phe Phe Thr Val Leu Phe Ala Ile Gly Arg Leu Pro Gly
385             390             395             400

Trp Ile Ala His Tyr Arg Glu Gln Leu Gly Ala Ala Gly Asn Lys Ile
            405             410             415

Asn Arg Pro Arg Gln Val Tyr Thr Gly Asn Glu Ser Arg Lys Leu Val
            420             425             430

Pro Arg Glu Glu Arg
            435
```

<210> SEQ ID NO 26
<211> LENGTH: 1314
<212> TYPE: DNA
<213> ORGANISM: Artificial Sequence
<220> FEATURE:
<223> OTHER INFORMATION: gltA_M312I

<400> SEQUENCE: 26
atgtttgaaa gggatatcgt ggctactgat aacaacaagg ctgtcctgca ctaccccggt        60
ggcgagttcg aaatggacat catcgaggct tctgagggta caacggtgt tgtcctgggc        120

-continued

```
aagatgctgt ctgagactgg actgatcact tttgacccag gttatgtgag cactggctcc       180
accgagtcga agatcaccta catcgatggc gatgcgggaa tcctgcgtta ccgcggctat       240
gacatcgctg atctggctga gaatgccacc ttcaacgagg tttcttacct acttatcaac       300
ggtgagctac caaccccaga tgagcttcac aagtttaacg acgagattcg ccaccacacc       360
cttctggacg aggacttcaa gtcccagttc aacgtgttcc cacgcgacgc tcacccaatg       420
gcaaccttgg cttcctcggt taacattttg tctacctact accaggacca gctgaaccca       480
ctcgatgagg cacagcttga taaggcaacc gttcgcctca tggcaaaggt tccaatgctg       540
gctgcgtacg cacaccgcgc acgcaagggt gctccttaca tgtacccaga caactccctc       600
aatgcgcgtg agaacttcct gcgcatgatg ttcggttacc caaccgagcc atacgagatc       660
gacccaatca tggtcaaggc tctggacaag ctgctcatcc tgcacgctga ccacgagcag       720
aactgctcca cctccaccgt tcgtatgatc ggttccgcac aggccaacat gtttgtctcc       780
atcgctggtg gcatcaacgc tctgtccggc ccactgcacg gtggcgcaaa ccaggctgtt       840
ctggagatgc tcgaagacat caagagcaac cacggtggcg acgcaaccga gttcatgaac       900
aaggtcaaga acaaggaaga cggcgtccgc ctcatcggct tcggacaccg cgtttacaag       960
aactacgatc cacgtgcagc aatcgtcaag gagaccgcac acgagatcct cgagcacctc      1020
ggtggcgacg atcttctgga tctggcaatc aagctggaag aaattgcact ggctgatgat      1080
tacttcatct cccgcaagct ctacccgaac gtagacttct acaccggcct gatctaccgc      1140
gcaatgggct tcccaactga cttcttcacc gtattgttcg caatcggtcg tctgccagga      1200
tggatcgctc actaccgcga gcagctcggt gcagcaggca acaagatcaa ccgcccacgc      1260
caggtctaca ccggcaacga atcccgcaag ttggttcctc gcgaggagcg ctaa            1314
```

```
<210> SEQ ID NO 27
<211> LENGTH: 42
<212> TYPE: DNA
<213> ORGANISM: Artificial Sequence
<220> FEATURE:
<223> OTHER INFORMATION: primer

<400> SEQUENCE: 27
gtgaattcga gctcggtacc cgcgggaatc ctgcgttacc gc                          42

<210> SEQ ID NO 28
<211> LENGTH: 42
<212> TYPE: DNA
<213> ORGANISM: Artificial Sequence
<220> FEATURE:
<223> OTHER INFORMATION: primer

<400> SEQUENCE: 28
tgtaaacgcg gtgtccgaag ccgatgaggc ggacgccgtc tt                          42

<210> SEQ ID NO 29
<211> LENGTH: 42
<212> TYPE: DNA
<213> ORGANISM: Artificial Sequence
<220> FEATURE:
<223> OTHER INFORMATION: primer

<400> SEQUENCE: 29
aagacggcgt ccgcctcatc ggcttcggac accgcgttta ca                          42

<210> SEQ ID NO 30
```

-continued

```
<211> LENGTH: 42
<212> TYPE: DNA
<213> ORGANISM: Artificial Sequence
<220> FEATURE:
<223> OTHER INFORMATION: primer

<400> SEQUENCE: 30
ggtcgactct agaggatccc cttagcgctc ctcgcgagga ac                          42

<210> SEQ ID NO 31
<211> LENGTH: 436
<212> TYPE: PRT
<213> ORGANISM: Artificial Sequence
<220> FEATURE:
<223> OTHER INFORMATION: IlvA_WT

<400> SEQUENCE: 31

Met Ser Glu Thr Tyr Val Ser Glu Lys Ser Pro Gly Val Met Ala Ser
1               5                   10                  15

Gly Ala Glu Leu Ile Arg Ala Ala Asp Ile Gln Thr Ala Gln Ala Arg
            20                  25                  30

Ile Ser Ser Val Ile Ala Pro Thr Pro Leu Gln Tyr Cys Pro Arg Leu
        35                  40                  45

Ser Glu Glu Thr Gly Ala Glu Ile Tyr Leu Lys Arg Glu Asp Leu Gln
    50                  55                  60

Asp Val Arg Ser Tyr Lys Ile Arg Gly Ala Leu Asn Ser Gly Ala Gln
65                  70                  75                  80

Leu Thr Gln Glu Gln Arg Asp Ala Gly Ile Val Ala Ala Ser Ala Gly
                85                  90                  95

Asn His Ala Gln Gly Val Ala Tyr Val Cys Lys Ser Leu Gly Val Gln
            100                 105                 110

Gly Arg Ile Tyr Val Pro Val Gln Thr Pro Lys Gln Lys Arg Asp Arg
            115                 120                 125

Ile Met Val His Gly Gly Glu Phe Val Ser Leu Val Val Thr Gly Asn
        130                 135                 140

Asn Phe Asp Glu Ala Ser Ala Ala Ala His Glu Asp Ala Glu Arg Thr
145                 150                 155                 160

Gly Ala Thr Leu Ile Glu Pro Phe Asp Ala Arg Asn Thr Val Ile Gly
                165                 170                 175

Gln Gly Thr Val Ala Ala Glu Ile Leu Ser Gln Leu Thr Ser Met Gly
            180                 185                 190

Lys Ser Ala Asp His Val Met Val Pro Val Gly Gly Gly Gly Leu Leu
        195                 200                 205

Ala Gly Val Val Ser Tyr Met Ala Asp Met Ala Pro Arg Thr Ala Ile
    210                 215                 220

Val Gly Ile Glu Pro Ala Gly Ala Ala Ser Met Gln Ala Ala Leu His
225                 230                 235                 240

Asn Gly Gly Pro Ile Thr Leu Glu Thr Val Asp Pro Phe Val Asp Gly
                245                 250                 255

Ala Ala Val Lys Arg Val Gly Asp Leu Asn Tyr Thr Ile Val Glu Lys
            260                 265                 270

Asn Gln Gly Arg Val His Met Met Ser Ala Thr Glu Gly Ala Val Cys
        275                 280                 285

Thr Glu Met Leu Asp Leu Tyr Gln Asn Glu Gly Ile Ile Ala Glu Pro
    290                 295                 300

Ala Gly Ala Leu Ser Ile Ala Gly Leu Lys Glu Met Ser Phe Ala Pro
305                 310                 315                 320
```

-continued

```
Gly Ser Val Val Val Cys Ile Ile Ser Gly Gly Asn Asn Asp Val Leu
            325                 330                 335

Arg Tyr Ala Glu Ile Ala Glu Arg Ser Leu Val His Arg Gly Leu Lys
            340                 345                 350

His Tyr Phe Leu Val Asn Phe Pro Gln Lys Pro Gly Gln Leu Arg His
        355                 360                 365

Phe Leu Glu Asp Ile Leu Gly Pro Asp Asp Asp Ile Thr Leu Phe Glu
    370                 375                 380

Tyr Leu Lys Arg Asn Asn Arg Glu Thr Gly Thr Ala Leu Val Gly Ile
385                 390                 395                 400

His Leu Ser Glu Ala Ser Gly Leu Asp Ser Leu Leu Glu Arg Met Glu
            405                 410                 415

Glu Ser Ala Ile Asp Ser Arg Arg Leu Glu Pro Gly Thr Pro Glu Tyr
            420                 425                 430

Glu Tyr Leu Thr
        435
```

```
<210> SEQ ID NO 32
<211> LENGTH: 1311
<212> TYPE: DNA
<213> ORGANISM: Artificial Sequence
<220> FEATURE:
<223> OTHER INFORMATION: ilvA_WT

<400> SEQUENCE: 32
atgagtgaaa catacgtgtc tgagaaaagt ccaggagtga tggctagcgg agcggagctg      60
attcgtgccg ccgacattca aacggcgcag gcacgaattt cctccgtcat tgcaccaact     120
ccattgcagt attgccctcg tctttctgag gaaaccggag cggaaatcta ccttaagcgt     180
gaggatctgc aggatgttcg ttcctacaag atccgcggtg cgctgaactc tggagcgcag     240
ctcacccaag agcagcgcga tgcaggtatc gttgccgcat ctgcaggtaa ccatgcccag     300
ggcgtggcct atgtgtgcaa gtccttgggc gttcaggggac gcatctatgt tcctgtgcag     360
actccaaagc aaaagcgtga ccgcatcatg gttcacggcg agagtttgt ctccttggtg      420 gtcactggca ataacttcga cgaagcatcg gctgcagcgc atgaagatgc agagcgcacc     480
ggcgcaacgc tgatcgagcc tttcgatgct cgcaacaccg tcatcggtca gggcaccgtg     540
gctgctgaga tcttgtcgca gctgacttcc atgggcaaga gtgcagatca cgtgatggtt     600
ccagtcggcg gtggcggact tcttgcaggt gtggtcagct acatggctga tatggcacct     660
cgcactgcga tcgttggtat cgaaccagcg ggagcagcat ccatgcaggc tgcattgcac     720
aatggtggac caatcacttt ggagactgtt gatccctttg tggacggcgc agcagtcaaa     780
cgtgtcggag atctcaacta caccatcgtg agaagaacc agggtcgcgt gcacatgatg       840
agcgcgaccg agggcgctgt gtgtactgag atgctcgatc tttaccaaaa cgaaggcatc     900
atcgcggagc ctgctggcgc gctgtctatc gctgggttga aggaaatgtc ctttgcacct     960
ggttctgtcg tggtgtgcat catctctggt ggcaacaacg atgtgctgcg ttatgcggaa    1020
atcgctgagc gctccttggt gcaccgcggt ttgaagcact acttcttggt gaacttcccg    1080
caaaagcctg gtcagttgcg tcacttcctg aagatatcc tgggaccgga tgatgacatc     1140
acgctgtttg agtacctcaa gcgcaacaac cgtgagaccg gtactgcgtt ggtgggtatt    1200
cacttgagtg aagcatcagg attggattct ttgctggaac gtatggagga atcggcaatt    1260
gattcccgtc gcctcgagcc gggcacccct gagtacgaat acttgaccta a             1311
```

<210> SEQ ID NO 33
<211> LENGTH: 26
<212> TYPE: DNA
<213> ORGANISM: Artificial Sequence
<220> FEATURE:
<223> OTHER INFORMATION: primer

<400> SEQUENCE: 33
ggatccgact gagcctgggc aactgg                                         26

<210> SEQ ID NO 34
<211> LENGTH: 26
<212> TYPE: DNA
<213> ORGANISM: Artificial Sequence
<220> FEATURE:
<223> OTHER INFORMATION: primer

<400> SEQUENCE: 34
ggatccccgt caccgacacc tccaca                                         26

<210> SEQ ID NO 35
<211> LENGTH: 25
<212> TYPE: DNA
<213> ORGANISM: Artificial Sequence
<220> FEATURE:
<223> OTHER INFORMATION: primer

<400> SEQUENCE: 35
acatcacgct ggcagagtac ctcaa                                          25

<210> SEQ ID NO 36
<211> LENGTH: 25
<212> TYPE: DNA
<213> ORGANISM: Artificial Sequence
<220> FEATURE:
<223> OTHER INFORMATION: primer

<400> SEQUENCE: 36
ttgaggtact ctgccagcgt gatgt                                          25

<210> SEQ ID NO 37
<211> LENGTH: 436
<212> TYPE: PRT
<213> ORGANISM: Artificial Sequence
<220> FEATURE:
<223> OTHER INFORMATION: IlvA_T381A, F383A

<400> SEQUENCE: 37

Met Ser Glu Thr Tyr Val Ser Glu Lys Ser Pro Gly Val Met Ala Ser
1               5                   10                  15

Gly Ala Glu Leu Ile Arg Ala Ala Asp Ile Gln Thr Ala Gln Ala Arg
            20                  25                  30

Ile Ser Ser Val Ile Ala Pro Thr Pro Leu Gln Tyr Cys Pro Arg Leu
        35                  40                  45

Ser Glu Glu Thr Gly Ala Glu Ile Tyr Leu Lys Arg Glu Asp Leu Gln
    50                  55                  60

Asp Val Arg Ser Tyr Lys Ile Arg Gly Ala Leu Asn Ser Gly Ala Gln
65                  70                  75                  80

Leu Thr Gln Glu Gln Arg Asp Ala Gly Ile Val Ala Ala Ser Ala Gly
            85                  90                  95

Asn His Ala Gln Gly Val Ala Tyr Val Cys Lys Ser Leu Gly Val Gln
            100                 105                 110

```
Gly Arg Ile Tyr Val Pro Val Gln Thr Pro Lys Gln Lys Arg Asp Arg
        115             120             125

Ile Met Val His Gly Gly Glu Phe Val Ser Leu Val Val Thr Gly Asn
        130             135             140

Asn Phe Asp Glu Ala Ser Ala Ala Ala His Glu Asp Ala Glu Arg Thr
145             150             155             160

Gly Ala Thr Leu Ile Glu Pro Phe Asp Ala Arg Asn Thr Val Ile Gly
            165             170             175

Gln Gly Thr Val Ala Ala Glu Ile Leu Ser Gln Leu Thr Ser Met Gly
            180             185             190

Lys Ser Ala Asp His Val Met Val Pro Val Gly Gly Gly Gly Leu Leu
        195             200             205

Ala Gly Val Val Ser Tyr Met Ala Asp Met Ala Pro Arg Thr Ala Ile
        210             215             220

Val Gly Ile Glu Pro Ala Gly Ala Ala Ser Met Gln Ala Ala Leu His
225             230             235             240

Asn Gly Gly Pro Ile Thr Leu Glu Thr Val Asp Pro Phe Val Asp Gly
            245             250             255

Ala Ala Val Lys Arg Val Gly Asp Leu Asn Tyr Thr Ile Val Glu Lys
        260             265             270

Asn Gln Gly Arg Val His Met Met Ser Ala Thr Glu Gly Ala Val Cys
        275             280             285

Thr Glu Met Leu Asp Leu Tyr Gln Asn Glu Gly Ile Ile Ala Glu Pro
        290             295             300

Ala Gly Ala Leu Ser Ile Ala Gly Leu Lys Glu Met Ser Phe Ala Pro
305             310             315             320

Gly Ser Val Val Val Cys Ile Ile Ser Gly Gly Asn Asn Asp Val Leu
            325             330             335

Arg Tyr Ala Glu Ile Ala Glu Arg Ser Leu Val His Arg Gly Leu Lys
        340             345             350

His Tyr Phe Leu Val Asn Phe Pro Gln Lys Pro Gly Gln Leu Arg His
        355             360             365

Phe Leu Glu Asp Ile Leu Gly Pro Asp Asp Ile Ala Leu Ala Glu
        370             375             380

Tyr Leu Lys Arg Asn Asn Arg Glu Thr Gly Thr Ala Leu Val Gly Ile
385             390             395             400

His Leu Ser Glu Ala Ser Gly Leu Asp Ser Leu Leu Glu Arg Met Glu
            405             410             415

Glu Ser Ala Ile Asp Ser Arg Arg Leu Glu Pro Gly Thr Pro Glu Tyr
            420             425             430

Glu Tyr Leu Thr
        435

<210> SEQ ID NO 38
<211> LENGTH: 1311
<212> TYPE: DNA
<213> ORGANISM: Artificial Sequence
<220> FEATURE:
<223> OTHER INFORMATION: ilvA_T381A, F383A

<400> SEQUENCE: 38
atgagtgaaa catacgtgtc tgagaaaagt ccaggagtga tggctagcgg agcggagctg      60
attcgtgccg ccgacattca aacggcgcag gcacgaattt cctccgtcat tgcaccaact     120
ccattgcagt attgccctcg tctttctgag gaaaccggag cggaaatcta ccttaagcgt     180
```

-continued

```
gaggatctgc aggatgttcg ttcctacaag atccgcggtg cgctgaactc tggagcgcag      240
ctcacccaag agcagcgcga tgcaggtatc gttgccgcat ctgcaggtaa ccatgcccag      300
ggcgtggcct atgtgtgcaa gtccttgggc gttcagggac gcatctatgt tcctgtgcag      360
actccaaagc aaaagcgtga ccgcatcatg gttcacggcg agagtttgt ctccttggtg       420 gtcactggca ataacttcga cgaagcatcg gctgcagcgc atgaagatgc agagcgcacc      480
ggcgcaacgc tgatcgagcc tttcgatgct cgcaacaccg tcatcggtca gggcaccgtg      540
gctgctgaga tcttgtcgca gctgacttcc atgggcaaga gtgcagatca cgtgatggtt      600
ccagtcggcg gtggcggact tcttgcaggt gtggtcagct acatggctga tatggcacct      660
cgcactgcga tcgttggtat cgaaccagcg ggagcagcat ccatgcaggc tgcattgcac      720
aatggtggac caatcacttt ggagactgtt gatcccttg tggacggcgc agcagtcaaa       780
cgtgtcggag atctcaacta caccatcgtg gagaagaacc agggtcgcgt gcacatgatg      840
agcgcgaccg agggcgctgt gtgtactgag atgctcgatc tttaccaaaa cgaaggcatc      900
atcgcggagc ctgctggcgc gctgtctatc gctgggttga aggaaatgtc ctttgcacct      960
ggttctgtcg tggtgtgcat catctctggt ggcaacaacg atgtgctgcg ttatgcggaa      1020
atcgctgagc gctccttggt gcaccgcggt ttgaagcact acttcttggt gaacttcccg      1080
caaaagcctg gtcagttgcg tcacttcctg gaagatatcc tgggaccgga tgatgacatc      1140
gcgctggcag agtacctcaa gcgcaacaac cgtgagaccg gtactgcgtt ggtgggtatt      1200
cacttgagtg aagcatcagg attggattct ttgctggaac gtatggagga atcggcaatt      1260
gattcccgtc gcctcgagcc gggcacccct gagtacgaat acttgacccta a             1311
```

```
<210> SEQ ID NO 39
<211> LENGTH: 22
<212> TYPE: DNA
<213> ORGANISM: Artificial Sequence
<220> FEATURE:
<223> OTHER INFORMATION: primer

<400> SEQUENCE: 39
aacacgaccg gcatcccgtc gc                                               22

<210> SEQ ID NO 40
<211> LENGTH: 23
<212> TYPE: DNA
<213> ORGANISM: Artificial Sequence
<220> FEATURE:
<223> OTHER INFORMATION: primer

<400> SEQUENCE: 40
aaatcatttg agaaaactcg agg                                              23

<210> SEQ ID NO 41
<211> LENGTH: 45
<212> TYPE: DNA
<213> ORGANISM: Artificial Sequence
<220> FEATURE:
<223> OTHER INFORMATION: primer

<400> SEQUENCE: 41
gtgaattcga gctcggtacc caaatcattt gagaaaactc gaggc                     45

<210> SEQ ID NO 42
<211> LENGTH: 45
<212> TYPE: DNA
<213> ORGANISM: Artificial Sequence
```

-continued

```
<220> FEATURE:
<223> OTHER INFORMATION: primer

<400> SEQUENCE: 42
ggtgatcatc tcaacggtgg aacacaggtt gatgatcatt gggtt                    45

<210> SEQ ID NO 43
<211> LENGTH: 45
<212> TYPE: DNA
<213> ORGANISM: Artificial Sequence
<220> FEATURE:
<223> OTHER INFORMATION: primer

<400> SEQUENCE: 43
aacccaatga tcatcaacct gtgttccacc gttgagatga tcacc                    45

<210> SEQ ID NO 44
<211> LENGTH: 42
<212> TYPE: DNA
<213> ORGANISM: Artificial Sequence
<220> FEATURE:
<223> OTHER INFORMATION: primer

<400> SEQUENCE: 44
ggtcgactct agaggatccc caagaaggca acatcggaca gc                       42

<210> SEQ ID NO 45
<211> LENGTH: 21
<212> TYPE: DNA
<213> ORGANISM: Artificial Sequence
<220> FEATURE:
<223> OTHER INFORMATION: primer

<400> SEQUENCE: 45
atccattcaa tggagtctgc g                                              21

<210> SEQ ID NO 46
<211> LENGTH: 616
<212> TYPE: PRT
<213> ORGANISM: Artificial Sequence
<220> FEATURE:
<223> OTHER INFORMATION: leuA_P247C, R558H, G561D

<400> SEQUENCE: 46

Met Ser Pro Asn Asp Ala Phe Ile Ser Ala Pro Ala Lys Ile Glu Thr
1               5                   10                  15

Pro Val Gly Pro Arg Asn Glu Gly Gln Pro Ala Trp Asn Lys Gln Arg
            20                  25                  30

Gly Ser Ser Met Pro Val Asn Arg Tyr Met Pro Phe Glu Val Glu Val
        35                  40                  45

Glu Asp Ile Ser Leu Pro Asp Arg Thr Trp Pro Asp Lys Lys Ile Thr
    50                  55                  60

Val Ala Pro Gln Trp Cys Ala Val Asp Leu Arg Asp Gly Asn Gln Ala
65                  70                  75                  80

Leu Ile Asp Pro Met Ser Pro Glu Arg Lys Arg Arg Met Phe Glu Leu
                85                  90                  95

Leu Val Gln Met Gly Phe Lys Glu Ile Glu Val Gly Phe Pro Ser Ala
            100                 105                 110

Ser Gln Thr Asp Phe Asp Phe Val Arg Glu Ile Ile Glu Lys Gly Met
        115                 120                 125

Ile Pro Asp Asp Val Thr Ile Gln Val Leu Val Gln Ala Arg Glu His
    130                 135                 140
```

-continued

Leu Ile Arg Arg Thr Phe Glu Ala Cys Glu Gly Ala Lys Asn Val Ile
145                 150                 155                 160

Val His Phe Tyr Asn Ser Thr Ser Ile Leu Gln Arg Asn Val Val Phe
                165                 170                 175

Arg Met Asp Lys Val Gln Val Lys Lys Leu Ala Thr Asp Ala Ala Glu
            180                 185                 190

Leu Ile Lys Thr Ile Ala Gln Asp Tyr Pro Asp Thr Asn Trp Arg Trp
            195                 200                 205

Gln Tyr Ser Pro Glu Ser Phe Thr Gly Thr Glu Val Glu Tyr Ala Lys
        210                 215                 220

Glu Val Val Asp Ala Val Val Glu Val Met Asp Pro Thr Pro Glu Asn
225                 230                 235                 240

Pro Met Ile Ile Asn Leu Cys Ser Thr Val Glu Met Ile Thr Pro Asn
                245                 250                 255

Val Tyr Ala Asp Ser Ile Glu Trp Met His Arg Asn Leu Asn Arg Arg
            260                 265                 270

Asp Ser Ile Ile Leu Ser Leu His Pro His Asn Asp Arg Gly Thr Gly
            275                 280                 285

Val Gly Ala Ala Glu Leu Gly Tyr Met Ala Gly Ala Asp Arg Ile Glu
        290                 295                 300

Gly Cys Leu Phe Gly Asn Gly Glu Arg Thr Gly Asn Val Cys Leu Val
305                 310                 315                 320

Thr Leu Ala Leu Asn Met Leu Thr Gln Gly Val Asp Pro Gln Leu Asp
                325                 330                 335

Phe Thr Asp Ile Arg Gln Ile Arg Ser Thr Val Glu Tyr Cys Asn Gln
            340                 345                 350

Leu Arg Val Pro Glu Arg His Pro Tyr Gly Gly Asp Leu Val Phe Thr
            355                 360                 365

Ala Phe Ser Gly Ser His Gln Asp Ala Val Asn Lys Gly Leu Asp Ala
        370                 375                 380

Met Ala Ala Lys Val Gln Pro Gly Ala Ser Ser Thr Glu Val Ser Trp
385                 390                 395                 400

Glu Gln Leu Arg Asp Thr Glu Trp Glu Val Pro Tyr Leu Pro Ile Asp
                405                 410                 415

Pro Lys Asp Val Gly Arg Asp Tyr Glu Ala Val Ile Arg Val Asn Ser
            420                 425                 430

Gln Ser Gly Lys Gly Gly Val Ala Tyr Ile Met Lys Thr Asp His Gly
        435                 440                 445

Leu Gln Ile Pro Arg Ser Met Gln Val Glu Phe Ser Thr Val Val Gln
        450                 455                 460

Asn Val Thr Asp Ala Glu Gly Gly Glu Val Asn Ser Lys Ala Met Trp
465                 470                 475                 480

Asp Ile Phe Ala Thr Glu Tyr Leu Glu Arg Thr Ala Pro Val Glu Gln
                485                 490                 495

Ile Ala Leu Arg Val Glu Asn Ala Gln Thr Glu Asn Glu Asp Ala Ser
            500                 505                 510

Ile Thr Ala Glu Leu Ile His Asn Gly Lys Asp Val Thr Val Asp Gly
            515                 520                 525

Arg Gly Asn Gly Pro Leu Ala Ala Tyr Ala Asn Ala Leu Glu Lys Leu
        530                 535                 540

Gly Ile Asp Val Glu Ile Gln Glu Tyr Asn Gln His Ala His Thr Ser
545                 550                 555                 560

-continued

```
Asp Asp Asp Ala Glu Ala Ala Ala Tyr Val Leu Ala Glu Val Asn Gly
            565                 570                 575

Arg Lys Val Trp Gly Val Gly Ile Ala Gly Ser Ile Thr Tyr Ala Ser
        580                 585                 590

Leu Lys Ala Val Thr Ser Ala Val Asn Arg Ala Leu Asp Val Asn His
    595                 600                 605

Glu Ala Val Leu Ala Gly Gly Val
    610                 615

<210> SEQ ID NO 47
<211> LENGTH: 1851
<212> TYPE: DNA
<213> ORGANISM: Artificial Sequence
<220> FEATURE:
<223> OTHER INFORMATION: leuA_P247C, R558H, G561D

<400> SEQUENCE: 47
atgtctccta cgatgcatt catctccgca cctgccaaga tcgaaacccc agttgggcct      60
cgcaacgaag gccagccagc atggaataag cagcgtggct cctcaatgcc agttaaccgc     120
tacatgcctt tcgaggttga ggtagaagat atttctctgc cggaccgcac ttggccagat     180
aaaaaaatca ccgttgcacc tcagtggtgt gctgttgacc tgcgtgacgg caaccaggct     240
ctgattgatc cgatgtctcc tgagcgtaag cgccgcatgt ttgagctgct ggttcagatg     300
ggcttcaaag aaatcgaggt cggtttccct tcagcttccc agactgattt tgatttcgtt     360
cgtgagatca tcgaaaaggg catgatccct gacgatgtca ccattcaggt tctggttcag     420
gctcgtgagc acctgattcg ccgtactttt gaagcttgcg aaggcgcaaa aaacgttatc     480
gtgcacttct acaactccac ctccatcctg cagcgcaacg tggtgttccg catggacaag     540
gtgcaggtga agaagctggc taccgatgcc gctgaactaa tcaagaccat cgctcaggat     600
tacccagaca ccaactggcg ctggcagtac tcccctgagt ccttcaccgg cactgaggtt     660
gagtacgcca aggaagttgt ggacgcagtt gttgaggtca tggatccaac tcctgagaac     720
ccaatgatca tcaacctgtg ttccaccgtt gagatgatca cccctaacgt ttacgcagac     780
tccattgaat ggatgcaccg caatctaaac cgtcgtgatt ccattatcct gtccctgcac     840
ccgcacaatg accgtggcac cggcgttggc gcagctgagc tgggctacat ggctggcgct     900
gaccgcatcg aaggctgcct gttcggcaac ggcgagcgca ccggcaacgt ctgcctggtc     960
accctggcac tgaacatgct gacccagggc gttgaccctc agctggactt caccgatata    1020
cgccagatcc gcagcaccgt tgaatactgc aaccagctgc gcgttcctga cgccaccca    1080 tacggcggtg acctggtctt caccgctttc tccggttccc accaggacgc tgtgaacaag    1140
ggtctggacg ccatggctgc caaggttcag ccaggtgcta gctccactga gtttcttgg    1200 gagcagctgc gcgacaccga atgggaggtt ccttacctgc ctatcgatcc aaaggatgtc    1260
ggtcgcgact acgaggctgt tatccgcgtg aactcccagt ccggcaaggg cggcgttgct    1320
tacatcatga agaccgatca cggtctgcag atccctcgct ccatgcaggt tgagttctcc    1380
accgttgtcc agaacgtcac cgacgctgag ggcggcgagg tcaactccaa ggcaatgtgg    1440
gatatcttcg ccaccgagta cctggagcgc accgcaccag ttgagcagat cgcgctcgc    1500 gtcgagaacg ctcagaccga aaacgaggat gcatccatca ccgccgagct catccacaac    1560
ggcaaggacg tcaccgtcga tggccgcggc aacggcccac tggccgctta cgccaacgcg    1620
ctggagaagc tgggcatcga cgttgagatc caggaataca accagcacgc ccacacctcg    1680
gatgacgatg cagaagcagc cgcctacgtg ctggctgagg tcaacggccg caaggtctgg    1740
```

-continued

```
ggcgtcggca tcgctggctc catcacctac gcttcgctga aggcagtgac ctccgccgta    1800
aaccgcgcgc tggacgtcaa ccacgaggca gtcctggctg gcggcgttta a              1851
```